United States Patent [19]
Trevino et al.

[11] Patent Number: 5,798,091
[45] Date of Patent: Aug. 25, 1998

[54] STABILIZED GAS EMULSION CONTAINING PHOSPHOLIPID FOR ULTRASOUND CONTRAST ENHANCEMENT

[75] Inventors: Leo A. Trevino; Ernest George Schutt, both of San Diego; David H. Klein, Carlsbad; Thomas E. Tarara, San Diego; Jeffry G. Weers, San Diego; Alexey Kabalnov, San Diego, all of Calif.

[73] Assignee: Alliance Pharmaceutical Corp., San Diego, Calif.

[21] Appl. No.: 395,680

[22] Filed: Feb. 28, 1995

Related U.S. Application Data

[63] Continuation-in-part of Ser. No. 284,083, Aug. 1, 1994, Pat. No. 5,605,673, which is a continuation-in-part of Ser. No. 99,953, Jul. 30, 1993, Pat. No. 5,414,600.

[51] Int. Cl.$^6$ ........................................... A61B 8/13
[52] U.S. Cl. .................. 424/9.52; 424/9.51; 128/662.02
[58] Field of Search ........................ 424/9.52, 450, 424/9.51; 128/662.02

[56] References Cited

U.S. PATENT DOCUMENTS

| | | | |
|---|---|---|---|
| 4,276,885 | 7/1981 | Tickner et al. | 128/660 |
| 4,466,442 | 8/1984 | Hilmann et al. | 128/662 |
| 4,613,326 | 9/1986 | Szwarc | 604/89 |
| 4,657,756 | 4/1987 | Rasor et al. | 424/9 |
| 4,684,479 | 8/1987 | D'Arrigo | 252/307 |

(List continued on next page.)

FOREIGN PATENT DOCUMENTS

| | | |
|---|---|---|
| 92/11547 | 9/1994 | Australia. |
| 0123235 | 10/1984 | European Pat. Off. |
| 0131540A2 | 1/1985 | European Pat. Off. |
| 0231091 | 8/1987 | European Pat. Off. |
| 0279379 | 8/1988 | European Pat. Off. |

(List continued on next page.)

OTHER PUBLICATIONS

Mattery, R.F., M.D., *Perfluorocytylbromide: A Liver/Spleen--Specific and Tumor–Imaging Ultrasound Contrast Material, Radiology,* 145(3):759–762 (Dec. 1992).

N. de Jong, et al., "Principles and Recent Developments in Ultrasound Contrast Agents", *Ultrasonics,* 29:324–330, 1991.

Greer, "First Ultrasound Contrast Agent Awaits OK from FDA", *Advance for Radiologic Science Professionals,* pp. 3–5, 1993.

Kitagawa, et al. Biological Abstracts 63: 6392 (1977).

Keough, et al. Biological Abstracts 81: 105308 (1986).

Matsuda, et al. "Contrast Echocardiography of the Left Heart by Intravenous Injection of Perfluorochemical Emulsion", J. of Cardiography 13(4): 1021–1028 (1983).

Sunamoto, et al. "Liposomal Membranes" J. Biochem 88: 1219–1226 (1980).

*Primary Examiner*—Gary E. Hollinden
*Attorney, Agent, or Firm*—Knobbe, Martens Olson & Bear, LLP

[57] ABSTRACT

A gas emulsion forming composition comprising a dry, hollow, particulate, approximately microspherical material permeated with a gas or gas mixture, which upon dissolution in aqueous liquid forms a gas emulsion comprising a plurality of bubbles surrounded by a layer of at least a first and a second surfactant, wherein the first surfactant consists essentially of a phospholipid or mixture of phospholipids having at least one acyl chain which comprises at least 10 carbon atoms, and comprising at least about 5% w/w of total surfactant, and wherein the second surfactant may or may not be a phospholipid and is more water soluble than the first surfactant; kits for preparing such microbubbles; and methods for using such microbubbles as contrast agents.

35 Claims, 2 Drawing Sheets

5,798,091
Page 2

U.S. PATENT DOCUMENTS

| | | | |
|---|---|---|---|
| 4,718,433 | 1/1988 | Feinstein | 128/660 |
| 4,774,958 | 10/1988 | Feinstein | 128/660.01 |
| 4,832,941 | 5/1989 | Berwing et al. | 424/9 |
| 4,844,882 | 7/1989 | Widder et al. | 424/9 |
| 4,898,734 | 2/1990 | Mathiowitz et al. | 424/426 |
| 4,904,479 | 2/1990 | Illum | 424/490 |
| 4,925,678 | 5/1990 | Ranney | 424/493 |
| 4,927,623 | 5/1990 | Long, Jr. | 424/5 |
| 4,957,656 | 9/1990 | Cerny et al. | 252/311 |
| 5,088,499 | 2/1992 | Unger | 128/662.02 |
| 5,108,759 | 4/1992 | Ranney | 424/493 |
| 5,123,414 | 6/1992 | Unger | 182/654 |
| 5,141,738 | 8/1992 | Rasor et al. | 424/2 |
| 5,149,319 | 9/1992 | Unger | 604/22 |
| 5,155,215 | 10/1992 | Ranney | 536/16 |
| 5,186,922 | 2/1993 | Shell et al. | 128/654 |
| 5,196,183 | 3/1993 | Yudelson et al. | 424/9 |
| 5,205,287 | 4/1993 | Erbel et al. | 128/632 |
| 5,205,290 | 4/1993 | Unger | 128/653.4 |
| 5,271,928 | 12/1993 | Schneider et al. | 424/9 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,333,613 | 8/1994 | Tickner et al. | 128/662.02 |
| 5,334,381 | 8/1994 | Unger | 424/9 |
| 5,348,016 | 9/1994 | Unger et al. | 128/662.02 |
| 5,352,435 | 10/1994 | Unger | 424/9 |
| 5,352,436 | 10/1994 | Wheatley et al. | 42/9 |
| 5,376,380 | 12/1994 | Kikuchi et al. | 424/450 |
| 5,393,524 | 2/1995 | Quay | 424/9 |
| 5,556,610 | 9/1996 | Yan et al. | 424/9 |
| 5,558,094 | 9/1996 | Quay | 128/662.02 |
| 5,558,853 | 9/1996 | Quay | 424/9 |
| 5,558,854 | 9/1996 | Quay | 424/9 |
| 5,558,855 | 9/1996 | Quay | 424/9 |
| 5,558,856 | 9/1996 | Klaveness et al. | 424/9.37 |
| 5,558,857 | 9/1996 | Klaveness et al. | 424/9.52 |

FOREIGN PATENT DOCUMENTS

| | | |
|---|---|---|
| 0358246 | 3/1990 | European Pat. Off. |
| 0554213 | 8/1993 | European Pat. Off. |
| 0606613A1 | 7/1994 | European Pat. Off. |
| 0458745B1 | 9/1994 | European Pat. Off. |
| WO8905160 | 6/1989 | WIPO |
| WO 91/09629 | 7/1991 | WIPO |
| WO 91/12823 | 9/1991 | WIPO |
| WO91/15999 | 10/1991 | WIPO |
| 9211873 | 7/1992 | WIPO |
| WO9300930 | 7/1992 | WIPO |
| WO 92/22247 | 12/1992 | WIPO |
| WO9222249 | 12/1992 | WIPO |
| WO 93/02712 | 2/1993 | WIPO |
| WO9303671 | 3/1993 | WIPO |
| WO 93/05819 | 4/1993 | WIPO |
| WO 93/06869 | 4/1993 | WIPO |
| WO9325242 | 12/1993 | WIPO |
| WO9401140 | 1/1994 | WIPO |
| WO9406477 | 3/1994 | WIPO |
| WO9408707 | 4/1994 | WIPO |
| WO9409703 | 5/1994 | WIPO |
| WO9409829 | 5/1994 | WIPO |
| WO9416739 | 8/1994 | WIPO |
| WO9421175 | 9/1994 | WIPO |
| WO9428797 | 12/1994 | WIPO |
| WO9428939 | 12/1994 | WIPO |
| 9628090 | 9/1996 | WIPO |

5,798,091

1

STABILIZED GAS EMULSION CONTAINING PHOSPHOLIPID FOR ULTRASOUND CONTRAST ENHANCEMENT

CROSS REFERENCE TO RELATED APPLICATIONS

This is a continuation-in-part of U.S. application Ser. No. 08/284,083, filed Aug. 1, 1994 U.S. Pat. No. 5,605,673, which is a continuation-in-part of U.S. application Ser. No. 08/099,953, filed Jul. 30, 1993 U.S. Pat. No. 5,414,600.

BACKGROUND OF THE INVENTION

1. Field of the Invention

The present invention includes a method for preparing stable, long-lived gas emulsions for ultrasound contrast enhancement and other uses, and to compositions of the gas emulsions so prepared.

2. Background of the Art

Ultrasound technology provides an important and more economical alternative to imaging techniques which use ionizing radiation. While numerous conventional imaging technologies are available, e.g., magnetic resonance imaging (MRI), computerized tomography (CT), and positron emission tomography (PET), each of these techniques use extremely expensive equipment. Moreover, CT and PET utilize ionizing radiation. Unlike these techniques, ultrasound imaging equipment is relatively inexpensive. Moreover, ultrasound imaging does not use ionizing radiation.

Ultrasound imaging makes use of differences in tissue density and composition that affect the reflection of sound waves by those tissues. Images are especially sharp where there are distinct variations in tissue density or compressibility, such as at tissue interfaces. Interfaces between solid tissues, the skeletal system, and various organs and/or tumors are readily imaged with ultrasound.

Accordingly, in many imaging applications ultrasound performs suitably without use of contrast enhancement agents; however, for other applications, such as visualization of flowing blood, there have been ongoing efforts to develop such agents to provide contrast enhancement. One particularly significant application for such contrast agents is in the area of perfusion imaging. Such ultrasound contrast agents could improve imaging of flowing blood in the heart muscle, kidneys, liver, and other tissues. This, in turn, would facilitate research, diagnosis, surgery, and therapy related to the imaged tissues. A blood pool contrast agent would also allow imaging on the basis of blood content (e.g., tumors and inflamed tissues) and would aid in the visualization of the placenta and fetus by enhancing only the maternal circulation.

A variety of ultrasound contrast enhancement agents have been proposed. The most successful agents have generally consisted of dispersions of small bubbles of gas that can be injected intravenously. Most typically, the bubbles are injected into the bloodstream of a living body to be imaged. The bubbles then provide a physical object in the flowing blood that is of a different density and a much higher compressibility than the surrounding fluid tissue and blood. As a result, these bubbles can easily be imaged with ultrasound. To traverse blood vessels, the bubbles should be less than 10 μm in diameter and have been called microbubbles. Microbubbles may be formed in a liquid in a variety of different ways. Simple examples are vigorous agitation or by forcing of a gas into a liquid through a small orifice. In the absence of additional ingredients, the gas will be in direct contact with the condensed medium (i.e., naked bubbles). However, such bubbles tend to shrink rapidly due to the diffusion of the trapped gas into the surrounding liquid. In addition, "naked" microbubbles have been shown to produce adverse responses such as the activation of complement (See, for example, K. A. Shastri et al. (1991) *Undersea Biomed. Res.*, 18, 157). Attempts to lengthen the life of microbubbles to increase their usefulness have focused on the addition of stabilizing agents which can enclose the gas bubbles, retarding the diffusion of the gas into the surrounding liquid.

Most microbubble compositions have failed to provide contrast enhancement that lasts even a few seconds, let alone minutes. This greatly limits their usefulness. Microbubbles have therefore been "constructed" in various manners in an attempt to increase their effective contrast enhancement life. Various avenues have been pursued such as the use of gelatins or albumin microspheres that are initially formed in liquid suspension, and which entrap gas during solidification. However, solid phase shells that encapsulate gases have generally proven too fragile or too permeable to the gas to have satisfactory in vivo life. Furthermore, thick shells (e.g., albumin, sugar, or other viscous materials) reduce the compressibility of the bubbles, thereby reducing their echogenicity during the short time they can exist. Solid particles or liquid emulsion droplets that evolve gas or boil when injected (as in Quay, PCT/US94/00422) pose the danger of supersaturating the blood with the gas or vapor. This will lead to a small number of large embolizing bubbles forming at the few available nucleation sites rather than the intended large number of small bubbles. In addition, bubbles created in vivo in this way will be "naked", and consequently will have the complement activation problem described above.

The use of surfactants as stabilizing agents for gas bubble dispersions has also been explored. Surfactants are materials which tend to form an interfacial layer at the interface of a polar substance with a non-polar substance. Their "surface active" behavior arises from the existence of both a hydrophilic region (often comprising one end which is usually referred to as the "head"), which tends to associate with the polar substance, and a hydrophobic region (often comprising the other end which is usually referred to as the "tail"), which tends to associate with the non-polar substance. When established, the interfacial layer affects the characteristics of the polar/non-polar interface. When surfactants are present, the gas may be separated from the liquid by an interfacial layer which may be comprised of a wide variety of surfactant materials.

Some surfactant-containing contrast enhancement agents entrap gas bubbles in another manner, e.g., in the aqueous core of liposomes. Liposomes are more or less spherical "bags" comprised of an aqueous core bounded by one or more concentric, closed, bimolecular phospholipid layers. Phospholipids, being natural components of cell membranes, are also well known for surfactant properties. In U.S. Pat. No. 5,334,381 to Unger, liposomes containing gas bubbles are created via several different mechanisms. Also, U.S. Pat. No. 4,900,540 to Ryan et al. discloses phospholipid liposomes which contain a gas or gas precursor. Presumably, the gas bubbles trapped inside the liposomes leak out slowly, thereby increasing the efficacy of the contrast agent. It may be noted that this use of a surfactant does not involve the presence of an interfacial layer of surfactant at the gas/liquid interface. Rather, small gas bubbles are trapped in a larger volume of aqueous liquid that is itself bounded by the uni- or multi-lamellar liposomal structure.

Surfactant containing contrast agents may utilize liposomes in other ways. For example, in U.S. Pat. Nos. 5,380,519 and 5,271,928 to Schneider et al., microbubbles prepared from freeze dried liposomes are described. According to this disclosure, reconstitution in water of a dry, pulverulent formulation created by lyophilizing a liposome suspension creates a dispersion of gas bubbles in suspension with water-filled liposomes. The microbubbles so prepared are stated to be surrounded by a "rather evanescent" envelope of surfactant. Although it would generally be expected that such an evanescent surfactant layer would not have persistence, and that such microbubbles would therefore not be stable for an extended period of time, Schneider et al. theorize that the laminated surfactant in or from the neighboring water-filled liposomes stabilizes the gas present in the system in the form of microbubbles.

It is readily appreciated that a liposome dependent contrast enhancement agent requires the prior formation of liposomes, and therefore limits the main component of stabilizing surfactant to a type which is capable of forming liposomes. Moreover, liposome preparation involves sophisticated and time consuming manufacturing.

Even in the presence of stabilizing compounds or structures, the entrapped gases are under increased pressure in the bubble due to the surface tension of the surrounding surfactant, as described by the Laplace equation ($\Delta P = 2\gamma/r$). This increased pressure further facilitates shrinkage and disappearance of the bubble as the gas moves from a high pressure area (in the bubble) to a lower pressure environment (in either the surrounding liquid which is not saturated with gas at this elevated pressure, or into a larger diameter, lower pressure bubble).

One proposal for dealing with such problems is outlined in Quay, PCT/US92/07250. Quay forms bubbles using gases selected on the basis of being a gas at body temperature (37° C.) and having reduced water solubility, higher density, and reduced gas diffusivity in solution in comparison to air. Although reduced water solubility and diffusivity can affect the rate at which the gas leaves the bubble, numerous problems remain with the Quay bubbles. Forming bubbles of sufficiently small diameter (e.g., 3–5 μm) requires high energy input. This is a disadvantage in that sophisticated bubble preparation systems must be provided at the site of use. Moreover, The Quay gas selection criteria are incorrect in that they fail to consider certain major causes of bubble shrinkage, namely, the effects of bubble surface tension, surfactants and gas osmotic effects, and these errors result in the inclusion of certain unsuitable gases and the exclusion of certain optimally suitable gases.

Accordingly, a need exists in the art for compositions, and a method to prepare such compositions, that provide, or utilize, a longer life contrast enhancement agent that is biocompatible, easily prepared, and provides superior contrast enhancement in ultrasound imaging.

SUMMARY OF THE INVENTION

In accordance with the present invention, there is provided a gas emulsion ultrasound contrast enhancement medium incorporating a mixture of surfactants as bubble stabilizing agents. At least one such surfactant is a hydrophobic phospholipid or mixture of phospholipids. At least a second surfactant is provided, which may or may not also be a phospholipid or mixture of phospholipids, but which is more hydrophilic than the phospholipid or combination of phospholipid provided as the first surfactant. Such a phospholipid stabilized gas emulsion has a prolonged longevity in vivo.

In one embodiment of the present invention a gas emulsion composition is prepared by first dispersing, in an aqueous solution, a hydrophilic monomer or polymer or combination thereof, a first and a second surfactant, and an inflating agent. The first surfactant is a phospholipid or mixture of phospholipids having at least one acyl chain comprising at least 10 carbon atoms and comprising at least about 5% w/w of total surfactant, and the second surfactant is more water soluble than said first surfactant.

The dispersion is then spray dried to evaporate the inflating agent and to create a dry, hollow, particulate, approximately microspherical material. This dry particulate material is exposed to at least a first gas, and then may be dissolved in an aqueous liquid, thereby forming an aqueous gas emulsion composition, where the composition comprises bubbles of the gas surrounded by a layer of the first and second surfactants, the stability of which is independent of liposomes.

The second surfactant can be comprised of a wide variety of materials. Some specific examples include fatty acids, salts of fatty acids, sugar esters of fatty acids, polyoxypropylene-polyoxyethylene copolymers, nonionic alkylglucosides, and polysorbates. Especially suitable gas emulsions are prepared when the second surfactant comprises a phospholipid or mixture of phospholipids having one or more acyl chains, wherein each acyl chain comprises no more than 14 carbon atoms. The hydrophilic monomer or polymer or combination thereof may be a starch.

The gas or combination of gases which permeates the dry particulate material may also be chosen from a wide variety of substances, including air, nitrogen, carbon dioxide, or other gases normally present in blood, and may also be an organic material such as a fluorocarbon. Preferably, one of the gases provided has a vapor pressure of less than 760 mm Hg at 37 degrees C. A particularly preferred embodiment uses nitrogen saturated with perfluorohexane.

The present invention also includes containers of gas permeated dry particulate gas emulsion forming compositions, and methods for imaging an object or body part or body cavity by introducing a phospholipid containing gas emulsion composition into the object or body part or body cavity and imaging at least a portion of the body by ultrasound.

DETAILED DESCRIPTION OF THE INVENTION

Figures 1, 2:
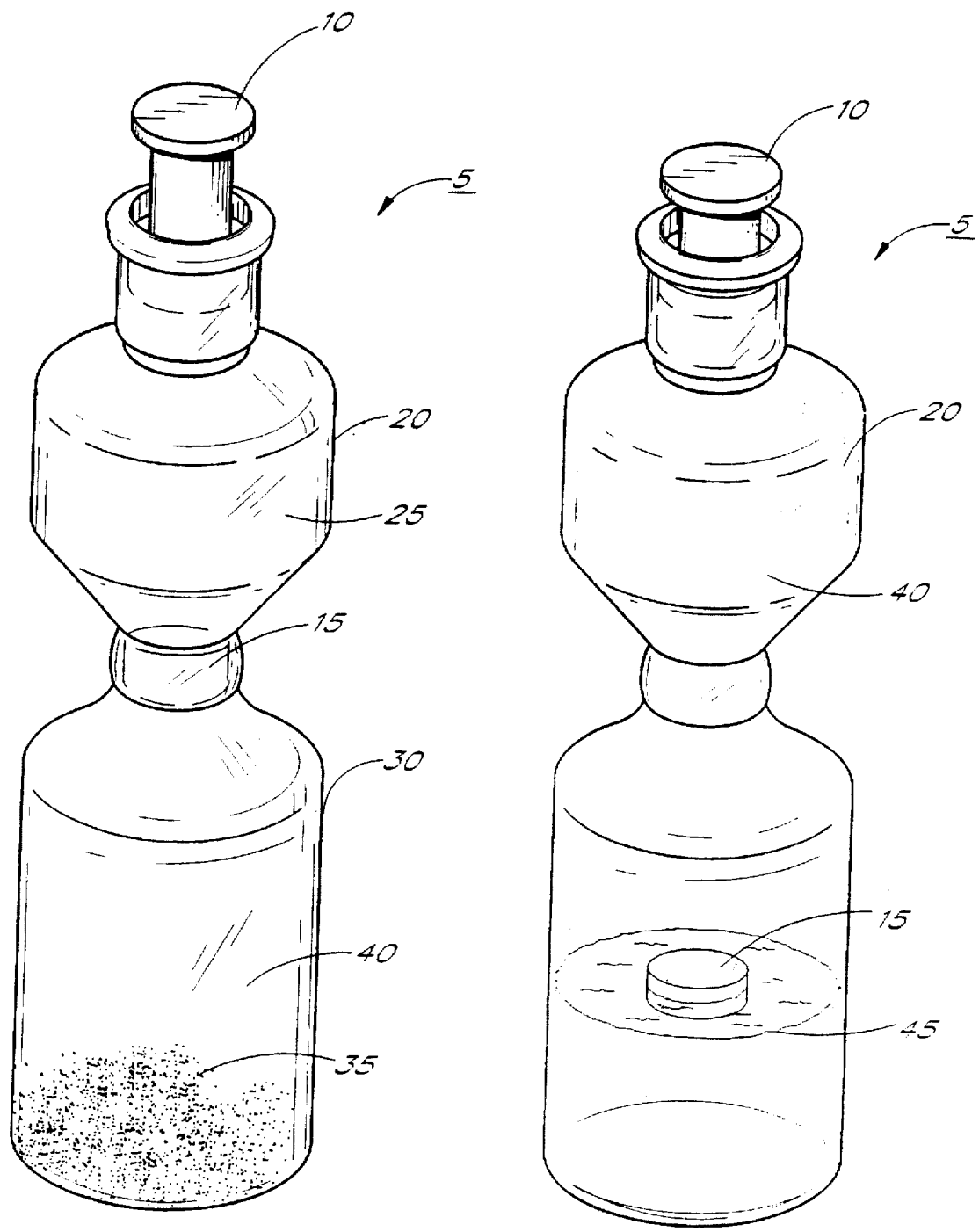
FIG. 1 is a perspective view of a two chamber vial containing a microbubble-forming preparation, with an aqueous solution in an upper chamber and solid and gaseous ingredients in a lower chamber.
FIG. 2 illustrates the vial of FIG. 1, where the aqueous solution has been mixed with the solid ingredients to form microbubbles for administration to a patient.

As used herein, microbubbles are considered to be bubbles of gas in an aqueous medium having a diameter between about 0.5 and 300 μm, preferably having a diameter no more than about 200, 100, or 50 μm. Microbubbles may or may not have a layer or coating at the gas/liquid interface. If present, the coating may be one or more molecules thick. Additionally, microbubbles may be trapped by a bimolecular layer (as in the case of unilamellar liposomes), or may be trapped by several layers of bilayers (multilamellar vesicles). Microbubbles may also be surrounded by more permanent shell-like structures such as denatured proteins. As emulsions are generally defined as a dispersion of two or more immiscible fluids stabilized by a surfactant interface, the gas dispersions of the present invention are in essence gas emulsions, with the discontinuous phase of the emulsion being a gas, rather than a liquid. Consequently, the term gas emulsion, as used herein, means a dispersion of a plurality of microbubbles of gas in an aqueous medium.

For intravascular use, optimum bubble size is determined by two competing concerns. Smaller bubbles are effective in circulating through small blood vessels and capillaries, but ultrasound echogenicity is strongly dependent upon bubble size. Suitable microbubbles for vascular ultrasound contrast enhancement are therefore preferably about 1–10 μm in diameter, with 3–5 μm especially preferred.

The present invention provides a gas dispersion or emulsion wherein the bubbles have a prolonged longevity in vivo, and that is suitable for use as ultrasound and magnetic resonance imaging (MRI) contrast enhancement agents. Typical ultrasound contrast enhancement agents exhibit contrast enhancement potential for only about one pass through the arterial system, or a few seconds to about a minute, and thus do not survive past the aorta in a patient following intravenous injection. In comparison, contrast agents prepared in accordance with the present invention continue to demonstrate contrast enhancements lives measured in multiple passes through the entire circulatory system of a patient following intravenous injection. Bubble lives of several minutes are easily demonstrated. Such lengthening of contrast enhancement potential during ultrasound is highly advantageous. In addition, the contrast enhancement agents of the invention provide superior imaging; for example, clear, vivid, and distinct images of blood flowing through the heart, liver, and kidneys are achieved. Thus small, nontoxic doses can be administered in a peripheral vein and used to enhance images of the entire body.

While bubbles have been shown to be the most efficient ultrasound scatterers for use in intravenous ultrasound contrast agents, their main practical drawback is the extremely short lifetime of the small (typically less than 5 microns diameter) bubbles required to pass through capillaries in suspension. This short lifetime is caused by the increased gas pressure inside the bubble, which results from the surface tension forces acting on the bubble. This elevated internal pressure increases as the diameter of the bubble is reduced. The increased internal gas pressure forces the gas inside the bubble to dissolve, resulting in bubble collapse as the gas is forced into solution. The Laplace equation, $\Delta P=2\gamma/r$, (where $\Delta P$ is the increased gas pressure inside the bubble, $\gamma$ is the surface tension of the bubble film, and r is the radius of the bubble) describes the pressure exerted on a gas bubble by the surrounding bubble surface or film. The Laplace pressure is inversely proportional to the bubble radius; thus, as the bubble shrinks, the Laplace pressure increases, increasing the rate of diffusion of gas out of the bubble and the rate of bubble shrinkage.

In one embodiment, the present invention contemplates gas dispersion compositions containing phospholipid surfactants having certain advantages over other surfactants and other phospholipid containing compositions. In a preferred embodiment, the composition includes two or more surfactants that are selected to assist in the creation of a large number of microbubbles, and also to optimally reduce the surface tension at the gas/liquid interface of the bubbles with the liquid. In addition, gases of low water solubility may advantageously constitute at least a part of the gas in the microbubbles. It has been found especially advantageous to use a phospholipid in conjunction with a second surfactant of higher water solubility as a stabilizing surfactant combination to improve gas entrapment.

The stability of a gas emulsion is highly dependent on the surface tension lowering properties of the surfactant used as the emulsifying agent. Phospholipids, as is known from their function as the main component of lung surfactant, are extremely efficient in this respect. They also readily form lamellar structures such as bilayer sheets and liposomes, although this characteristic is not necessary for stabilizing the gas dispersions of the present invention. Another determinant of gas emulsion stability is the gas itself, and its ability to stabilize via a gas osmotic effect as described below and in co-pending U.S. application Ser. No. 08/284, 083, incorporated herein by reference. This combination results in a surprisingly stable and practically useful microbubble.

Gas dispersion compositions according to the present invention may be prepared by spray drying an aqueous dispersion of a first surfactant comprising a phospholipid, preferably at least one additional co-surfactant (also referred to herein as the "second surfactant"), and a hydrophilic monomer or polymer or combination thereof. The aqueous starting material may optionally include salts and/or and an inflating agent. Spray drying such a solution according to the present invention results in the production of a dry, hollow, particulate, approximately microspherical material.

It was surprisingly discovered that a pre-formed spherical cavity composed of water soluble components (e.g. hydroxyethyl starch, salts) and a relatively water soluble surfactant (e.g. Pluronic F-68, Tween 20, dioctonoyl phosphotidyl choline) and a phospholipid (e.g. egg yolk phospholipid), when in the physical form produced by spray drying, can form remarkably stable microbubbles when rehydrated. The surfactant need not be present in liposomal or other lamellar form. This may be the result of water first contacting the inside surface of the spherical cavity (0.5–10 microns diameter) after percolating through the dissolving surfactants and structural agents resulting in the formation of a bubble of the desired size (the size of the cavity) surrounded initially by saturated surfactant solution and therefore having an optimal maximally packed surfactant coating. These bubbles are remarkably stable in-vivo even when filled with water soluble gases (e.g. air or nitrogen).

This process, as well as the dry and reconstituted products obtained thereby are explained and described in more detail below.

I. Preparing a Phospholipid-Containing Precursor Dispersion

For subsequent spray drying, a first aqueous solution containing a hydrophobic phospholipid as a first surfactant and at least one additional more hydrophilic surfactant is prepared. Preferably, the hydrophobic phospholipid has at least one acyl chain with a total of at least about 10 carbon atoms (e.g. a decanoyl phospholipid). In some embodiments, the phospholipid first surfactant will have acyl chains from about 10 or 14 to about 20 or 24 carbon atoms. For example, dipalmitoylphosphatidylcholine (comprising two acyl chains, each comprising 16 carbon atoms) may be used. The acyl chain may be hydrogenated or fluorinated. Other phospholipid head groups are also contemplated. For example, the phosphatidylserines, phosphatidylglycerols, or phosphatidylethanolamines will have properties suited to the present invention. Combinations of such phospholipids can also comprise the "first surfactant," as can naturally derived phospholipid products such as egg or soy lecithin, or lung surfactants. In addition, the phospholipid first surfactant may be supplemented with other highly water insoluble surfactants such as sucrose di-, tri-, and tetra-esters. Cholesterol may also supplement the first surfactant, and has been found useful in promoting stability when provided in a range from about 0.01 to 0.5 w/w cholesterol to phospholipid. Preferably, the acyl chains of the phospholipid are saturated, although unsaturated acyl groups are also within the scope of the present invention. The first surfactant is preferably provided in a range from about 0.005% to 20% w/v of the solution, most preferably in the range of 0.02% to 10% w/v.

The primary role of the hydrophobic first surfactant is to reduce the surface tension of formed microbubbles below equilibrium values. When relatively insoluble osmotic stabilizing gases are entrapped (described in detail below), a first surfactant with very low water solubility is required, because surface tension reduction to below equilibrium values is only possible when the surfactant diffuses more slowly than the entrapped stabilizing gas. To achieve suitably low surfactant solubilities, phospholipids with long acyl chains (i.e. comprising more than 10 carbon atoms) are particularly preferred.

The second surfactant is preferably more hydrophilic and faster diffusing than the long chain phospholipid comprising the first surfactant. The role of this second surfactant in the formation of a stable gas dispersion is likely related to a faster rate of dissolution upon reconstitution with water and more effective gas entrapment, thereby facilitating the creation of bubbles in the early stages of reconstitution, which is described further below. In this way, the faster diffusion rate of the second surfactant aids in creating a relatively durable and continuous film surrounding the gas upon reconstitution.

In the present invention, preferred second surfactants may be selected from the group consisting of phospholipids, phosphocholines, lysophospholipids, nonionic surfactants, neutral or anionic surfactants, fluorinated surfactants, which can be neutral or anionic, and combinations of such emulsifying or foaming agents. Some specific examples of surfactants which are useful as the second surfactant include block copolymers of polyoxypropylene and polyoxyethylene (an example of such class of compounds is Pluronic, such as Pluronic F-68), sugar esters, fatty alcohols, aliphatic amine oxides, hyaluronic acid aliphatic esters, hyaluronic acid aliphatic ester salts, dodecyl poly(ethyleneoxy)ethanol, nonylphenoxy poly(ethyleneoxy) ethanol, derivatized starches, hydroxy ethyl starch fatty acid esters, salts of fatty acids, commercial food vegetable starches, dextran fatty acid esters, sorbitol fatty acid esters, gelatin, serum albumins, and combinations thereof.

Also contemplated as a second surfactant are polyoxyethylene fatty acids esters, such as polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof. In addition, nonionic alkylglucosides such as Tweens®, Spans® and Brijs® are also within the scope of the present invention. The Spans include sorbitan tetraoleate, sorbitan tetrastearate, sorbitan tristearate, sorbitan tripalmitate, sorbitan trioleate, and sorbitan distearate. Tweens include polyoxyethylene sorbitan tristearate, polyoxyethylene sorbitan tripalmitate, polyoxyethylene sorbitan trioleate. The Brij family is another useful category of materials, which includes polyoxyethylene 10 stearyl ether. Anionic surfactants, particularly fatty acids (or their salts) having 6 to 24 carbon atoms, may also be used. One example of a suitable anionic surfactant is oleic acid, or its salt, sodium oleate. Cationic surfactants and their salts, such as dodecyltrimethylammonium chloride are also contemplated for use as second surfactants.

It will be appreciated from the foregoing that a wide range of second surfactants can be used. Indeed, virtually any surfactant (including those still to be developed) of higher water solubility and diffusivity than what is typically a longer chain phospholipid comprising the first surfactant can be used in the present invention. The optimum surfactant for a given application can be determined through empirical studies that do not require undue experimentation. Consequently, one practicing the art of the present invention should choose the surfactant based upon such properties as biocompatibility. It has been found to be advantageous to use as a co-surfactant a shorter chain phospholipid which is more hydrophilic than the first phospholipid. As a specific example, a first phospholipid having acyl chains with 12 or 14 carbon atoms may be provided with a second phospholipid as a co-surfactant having acyl chains with eight or ten carbon atoms.

It has been found especially advantageous to provide phospholipid comprising 12 carbon atom acyl chains as either the first or second surfactants. For example, a phospholipid with 12 carbon atom acyl chains may comprise the first surfactant, and a sugar ester or Pluronic compound can comprise the second surfactant. As another option, a phospholipid with 16 carbon atom acyl chains may comprise the first surfactant, and a phospholipid with 12 carbon atom acyl chains may comprise the second surfactant.

In addition to having excellent bubble formation and persistence qualities, microbubbles formed with phospholipid as both a first and co-surfactant can have superior properties in the area of metabolic elimination after in vivo injection, as well as minimizing undesirable in vivo responses such as the activation of complement, which can be a problem with prior art microbubbles. Gas emulsion compositions containing phospholipid surfactants with 12 or 14 carbon atom acyl chains appear to be especially advantageous in this regard.

It is believed that phospholipid-containing microbubbles are not only more biocompatible than those containing non-phospholipid surfactants, but also that they are more biocompatible than liposomes. That is, they apparently evade the reticuloendothelial system more effectively than liposomes, and are thus not cleared from circulation as quickly.

As was stated with regard to the first surfactant, the second or co-surfactant can comprise combinations of the surfactants described above. Preferably, prior to spray drying, the second surfactant is provided in a range of 0.005% to 20% w/v. It is not required that the first surfactant predominate the mix. Either the first or second surfactant may be provided in greater molarity and/or weight. Generally, the total surfactant in solution is about 0.01% to 20% w/v of solution.

Following the production of the aqueous solution of surfactant as described above, an inflating agent, preferably a fluorocarbon such as Freon 113, is added, creating a coarse suspension. The inflating agent can be any material that will turn to a gas during the spray drying process. The inflating agent is then dispersed throughout the surfactant solution, using, for instance, a commercially available microfluidizer at a pressure of about 5000 to 15,000 psi. In one preferred embodiment of the present invention, a high pressure homogenizer is used to make a conventional emulsion of Freon 113 in a phospholipid containing surfactant solution. This process forms a conventional emulsion comprised of submicron droplets of water immiscible Freon coated with a monomolecular layer of surfactant. Dispersion with this and other techniques are common and well known to those in the art.

The inclusion of an inflating agent in the solution to be spray-dried results in a greater ultrasound signal per gram of spray-dried powder by forming a greater number of hollow microspheres. The inflating agent nucleates steam bubble formulation within the atomized droplets of the solution entering the spray dryer as these droplets mix with the hot air stream within the dryer. Suitable inflating agents are those that supersaturate the solution within the atomized droplets with gas or vapor, at the elevated temperature of the drying droplets (approximately 100° C.). Suitable agents include:

1. Dissolved low-boiling (below 100° C.) solvents with limited miscibility with aqueous solutions, such as methylene chloride, acetone and carbon disulfide used to saturate the solution at room temperature.
2. A gas, e.g. $CO_2$ or $N_2$, used to saturate the solution at room temperature and elevated pressure (e.g. 3 bar). The droplets are then supersaturated with the gas at 1 atmosphere and 100° C.
3. Emulsions of immiscible low-boiling (below 100° C.) liquids such as Freon 113, perfluoropentane, perfluorohexane, perfluorobutane, pentane, butane, FC-11, FC-11B1, FC-11B2, FC-12B2, FC-21, FC-21B1, FC-21B2, FC-31B1, FC-113A, FC-122, FC-123, FC-132, FC-133, FC-141, FC-141B, FC-142, FC-151, FC-152, FC-1112, FC-1121 and FC-1131.

Inflating agents are added to the surfactant solution in quantities of about 0.5% to 10% v/v of the surfactant solution. Approximately 3% v/v inflating agent has been found to produce a spray dried powder which forms suitable microbubbles. The inflating agent is substantially evaporated during the spray drying process and thus is not present in the final spray-dried powder in more than trace quantities.

The aqueous precursor solution preferably includes a hydrophilic monomer or polymer or combination thereof. This can be combined with the surfactant solution, or, more preferably, formed as a separate solution and combined with the surfactant precursor solution just prior to spray drying.

The hydrophilic moiety can, for example, be a carbohydrate, such as glucose, lactose, or starch. Polymers such as PVA or PVP are also contemplated for use with the present invention. Various starches and derivatized starches have been found to be especially suitable. Particularly preferred starches for use in formation of microbubbles include those with a molecular weight of greater than about 500,000 daltons or a dextrose equivalency (DE) value of less than about 12. The DE value is a quantitative measurement of the degree of starch polymer hydrolysis. It is a measure of reducing power compared to a dextrose standard of 100. The higher the DE value, the greater the extent of starch hydrolysis. Such preferred starches include food grade vegetable starches of the type commercially available in the food industry, including those sold under the trademarks N-LOK and CAPSULE by National Starch and Chemical Co., (Bridgewater, N.J.); derivatized starches, such as hydroxyethyl starch (available under the trademarks HETASTARCH and HESPAN from du Pont Pharmaceuticals, M-Hydroxyethylstarch from Ajinimoto, Tokyo, Japan). (Note that short chain starches spray dry well and can be used to produce microbubbles, but are not preferred because those with a molecular weight less than about 500,000 do not stabilize the microbubbles. However, they can be used in the present invention in applications in which additional stabilization is not required.) The hydrophilic monomer or polymer is present in this embodiment of the precursor solution at a range of about 0.1% to 10% w/v of solution, with about 1% to 5% w/v having been found to be especially suitable.

Other optional components of this embodiment of the precursor solution are various salts or other agents within the aqueous phase. Such agents may advantageously include conventional viscosity modifiers, buffers such as phosphate buffers or other conventional biocompatible buffers or pH adjusting agents such as acids or bases, osmotic agents (to provide isotonicity, hyperosmolarity, or hyposmolarity). Preferred solutions have a pH of about 7 and are isotonic. These additional ingredients each typically comprise less than 5% w/v of solution. Examples of suitable salts include sodium phosphate (both monobasic and dibasic), sodium chloride, calcium phosphate, and other physiologically-acceptable salts.

II. Spray Drying

The surfactant/inflating agent emulsion is preferably combined with a solution of hydrophilic monomer/polymer and salts, of the type described above, and is spray dried to form a powder of dry, hollow, approximately microspherical structures. Commercially available spray dryers are well known to those in the art, and suitable settings for any particular precursor solution can be readily determined through standard empirical testing, with due reference to the examples that follow.

The "Niro Portable Spray Dryer", employed in Examples I-VII and IX-XII below, functions by atomizing a surfactant containing solution with a two fluid compressed air nozzle, which uses a high speed jet of compressed air to break the aqueous surfactant solution up into droplets ranging from 2 to 20 microns in diameter. These droplets are then injected into a stream of hot air (typically 200 to 375 degrees C.) at the top of the drying chamber. The surfactant solution droplets are then nearly instantaneously heated to their boiling point of approximately 100 degrees C. Although evaporative cooling prevents them from rising to a higher temperature, the temperature is still higher than the glass transition temperature of phospholipids and above the melting point of many other surfactants such as Poloxamer 188 and sucrose stearate.

The water at the surface of the droplet evaporates very rapidly, causing a buildup of the compounds which were dissolved in the atomized solution. When the solution contains a hydrophilic polymer such as hydroxyethyl starch (HES), a gel layer forms at the surface. Beneath the gel layer, a bubble of steam forms which inflates the gel sphere. As was described briefly above, the presence of an inflating agent comprising a sparingly soluble volatile solvent such as methylene chloride or a volatile immiscible solvent such as Freon 113 provides nucleation sites for early steam bubble formation, leading to more steam inflation and thinner walled hollow spheres.

During the drying process, water either migrates through pores in the gel layer to the surface of the sphere as a liquid, where it is vaporized, or it escapes from the sphere as steam through the same gel layer pores. Finally, the water trapped in the HES gel evaporates. During this phase of the drying process, evaporation and evaporative cooling are slowed, and the sphere rises in temperature to match the exit temperature of the spray drying chamber, typically 100 to 120 degrees C. The gel sphere shrinks as it is dehydrated to yield hollow porous spheres of approximately 1 to 10 μm in diameter, with shell thicknesses of approximately 0.2 μm. The spray dryer exit air stream carries the spheres to a cyclone separator where the powder is separated from the air stream by centrifugal force and directed into a product container.

For several reasons, the composite structure of the dried spherical surfactant/polymer composition is characterized as random with the substantial absence of lamellar forms. First, homogenization to form an emulsion with an inflating agent prior to spray drying deposits the surfactant in a monomolecular layer. Because the drying takes place in a small fraction of a second, the rapid entrapment of the surfactant in a concentrated polymer (e.g. HES) gel maintains the surfactants in approximately the physical state they were in prior to drying. Furthermore, during the spray drying process, the less water soluble surfactants (sucrose stearate, long chain phospholipids, etc.) are heated above their melting point or glass transition temperature in the presence of a more water soluble surfactant and are thereby incorporated into the matrix of the hydrophilic polymer. This is conducive to more random surfactant structures.

This spray dried composition, comprising gas-filled hollow microspheres, is an important product of the present invention. This product provides significant advantages over lyophilized liposome containing precursors. It is believed that the spherical structure of the present microbubble precursor material serves to quickly and uniformly form the relatively insoluble, relatively incompressible non-Newtonian viscoelastic surfactant film that is characteristic of preferred microbubbles of the present invention.

After spray drying is completed, the microspheres are packaged in a container with an appropriate gas. This gas fills the microspheres and becomes the gas entrapped in the microbubbles after reconstitution.

The various individual components of the microspheres preferably comprise the following proportions of the final spray dried product in % by weight:

| First phospholipid surfactant | 0.05% to 90% |
| Second surfactant | 0.05% to 90% |
| Hydrophilic structural material | 1% to 99% |
| Salts, buffer, etc. | 0% to 90% |

In particularly preferred embodiments, the composition has the following proportions in % by weight:

| First phospholipid surfactant | 0.1% to 10% |
| Second surfactant | 0.1% to 10% |
| Hydrophilic structural material | 10% to 60% |
| Salts, buffer, etc. | 10% to 60% |

Most preferably, the amount of the first surfactant (advantageously a phospholipid) is at least about 1%, preferably at least about 3%, 4%, or 5%, and most preferably at least about 7%, 8%, or 10% of the total surfactant, w/w. It may well constitute 25%, 50%, 75%, or 95% of the total surfactant, w/w, and embodiments lacking the second surfactant, while not preferred, are also contemplated.

In an alternative embodiment of the present invention, the composition of the precursor solution is such that a liposome-forming spray dried powder is prepared. Such precursor solutions can have, for example, the composition of U.S. Pat. No. 5,380,519 to Schneider et al, which is hereby incorporated by reference. We have discovered that the spray drying technique described herein for forming microbubble precursors of phospholipid-containing solutions is superior to the lyophilization of Schneider, et al, and that the resulting microbubbles seem to be much more stable than those formed of lyophilized material. Thus, in this one aspect of the invention, it is contemplated that the spray drying technique can be used to prepare dried liposome forming precursor that is then reconstituted to form microbubbles, as in Schneider et al, for use in echographic imaging techniques.

III. Reconstitution and Gas Selection

Upon reconstitution in an aqueous medium, the hydrophilic monomer or polymer that in some preferred embodiments provides structure to the shell, as well as the salts and any buffers, etc. which may be present quickly dissolve away, leaving behind a gas emulsion or dispersion comprising bubbles of gas which are surrounded by a layer of the surfactant which is left behind. The first phospholipid surfactant, and the more hydrophilic co-surfactant are hypothesized to perform different functions.

Without limitation to any particular theory of operation, the second surfactant (or co-surfactant) is apparently useful in aiding the dissolution of the water soluble structural materials, and may also diffuse quickly enough immediately upon reconstitution to "heal" surfactant free gaps which exist during shell dissolution. It has been found that reconstitution of microspherical powder containing in part a relatively water soluble surfactant in conjunction with a more hydrophobic surfactant produces a much higher number of bubbles per milliliter of enhancement agent than reconstituted powder containing only a single hydrophobic surfactant. Although the second relatively hydrophilic surfactant is apparently important in the transition from dried, hollow sphere to surfactant coated gas bubble, it is thought that the more hydrophobic first phospholipid is the most effective stabilizing agent after the bubbles are formed.

The gas dispersion thus created is therefore fundamentally different from prior contrast enhancement compositions containing phospholipid. As described above, the gas containing liposomes of Ryan and Unger do not involve surfactant layers at the gas/liquid interface of the bubbles, but involve essentially naked bubbles trapped in the aqueous cores of liposomes. This may be distinguished from the gas emulsion or microbubble dispersion of the present invention, wherein it appears (without being limited to any particular theory of operation) that small gas bubbles are surrounded by a relatively durable, nonevanescent layer of surfactant with orientation such that hydrophilic head groups are associated with the aqueous liquid, and hydrophobic tail groups are associated with the dispersed gas bubbles. Furthermore, in contrast with Schneider, et al., the gas dispersions of the present invention do not require the presence in solution of liposomes or other lamellar surfactant structures. In fact, gas dispersions with excellent in vivo stability may be prepared according to the present invention in which the surfactants used are incapable of forming liposomes. The absence of lamellar surfactant structures in solution does not significantly affect the efficacy of the contrast agents of the present invention. Additionally, it has been observed that the presence of a fluorocarbon osmotic stabilizer gas in the bubbles dramatically increases the stability of the gas dispersions of the present invention, whereas the presence of a fluorocarbon osmotic stabilizer has little effect on the stability of microbubbles produced from lyophilized liposomes. These differences in behavior further suggest (again, without being limited to any particular theory of operation) that the gas in the bubbles of the present invention is entrapped by a relatively durable, nonevanescent layer of surfactant with orientation such that the hydrophilic head groups are associated with the aqueous liquid, and the hydrophobic tail groups are associated with the dispersed gas bubbles.

Suitable bubbles containing air, nitrogen, or other gases normally present in blood may be created by reconstituting the above described spray dried microspheres in an aqueous medium. It has also been found that bubble life may be improved when a relatively water insoluble gas, such as a fluorocarbon, is made to permeate the dry microspheres prior to reconstitution. In this case, the invention will utilize a first gas or gases (a "primary modifier gas") that optionally is ordinarily present in normal blood and serum in combination with one or more additional second gases (a "gas osmotic agent or agents" or a "secondary gas") that act to regulate the osmotic pressure within the bubble. Through regulating the osmotic pressure of the bubble, the gas osmotic agent (defined herein as a single or mixture of chemical entities) exerts pressure within the bubble, aiding in preventing deflation. Optionally, the modifier gas may be a gas that is not ordinarily present in blood or serum. However, the modifier gas must be capable of diluting and maintaining the gas osmotic agent or agents at a partial pressure below the vapor pressure of the gas osmotic agent or agents while the gases in blood or other surrounding liquid diffuse into the bubble. In an aqueous medium, water vapor is not considered to be one of the "gases" in question. Similarly, when microbubbles are in a nonaqueous liquid medium, the vapor of that medium is not considered to be one of the "gases."

We have discovered that by adding a gas osmotic agent that has, for example, a reduced membrane permeability through the bubble's surface or reduced solubility in the external continuous phase liquid phase, the life of a bubble formed therewith may be increased.

This result is achieved through the entrapment, within the chosen gas emulsion, of a combination of gases, preferably a primary modifier gas or mixture of gases that will dilute a gas osmotic agent to a partial pressure less than the gas osmotic agent's vapor pressure until the modifier gas will exchange with gases normally present in the external medium. The gas osmotic agent or agents are generally relatively hydrophobic and relatively bubble membrane impermeable and also further possess the ability to develop gas osmotic pressures greater than 50, 75, or 100 Torr. In one preferred embodiment, the gas vapor pressure of the gas osmotic agent is preferably less than about 760 Torr at 37° C., preferably less than about 750, 740, 730, 720, 710, or 700 Torr, and in some embodiments less than about 650, 600, 500, or 400 Torr. In preferred embodiments, the vapor pressure of the primary modifier gas is at least 660 Torr at 37° C. and the vapor pressure of the gas osmotic agent is at least 100 Torr at 37° C.

The first gas and the second gas are respectively present in a molar ratio of about 1:100, 1:75, 1:50, 1:30, 1:20, or 1:10 to about 1000:1, 500:1, 250:1, 100:1, 75:1 or 50:1, and where the first gas has a vapor pressure of at least about (760-x) mm Hg at 37° C., where x is the vapor pressure of the second gas at 37° C., and where the vapor pressure of each of the first and second gases is greater than about 75 or 100 mm Hg at 37° C.

Gas emulsion or gas dispersion bubbles prepared in accordance with one preferred embodiment of the invention may also possess an additional advantageous property. In one such embodiment, mixtures of nonosmotic gases with osmotic stabilizing gases (or gas osmotic agents) are used to stabilize the resultant bubble size distribution during and immediately after production. Upon generation of the bubbles, the higher Laplace pressure in smaller bubbles causes diffusion through the liquid phase to the lower Laplace pressure larger bubbles. This causes the mean size distribution to increase above the capillary dimension limit of 5 microns over time. This is called disproportionation. when a mixture of a nonosmotic gas (e.g., air) is used with an osmotic vapor (e.g., $C_6F_{14}$) a slight reduction in volume of the smaller bubbles, due to air leaving the bubble, concentrates the osmotic gas and increases its osmotic pressure thus retarding further shrinkage while the larger bubbles increase in volume slightly, diluting the osmotic gas and retarding further growth.

An additional advantage of using a mixture of an extremely blood soluble gases (e.g., 87.5% by volume $CO_2$) and an osmotic gas mixture (e.g., 28% $C_6F_{14}$ vapor+72% air) is that, when injected, these bubbles rapidly shrink due to the loss of $CO_2$ to the blood. The bubbles, upon injection, will experience an 87.5% volume decrease due to loss of $CO_2$. This loss of $CO_2$ corresponds to a halving of the bubble diameter. Accordingly, one can prepare larger diameter bubbles (e.g., 9 μm), using simplified mechanical means, that will shrink to below 5 microns upon injection. In general, such a gas emulsion will initially be prepared where the first gas is present in a ratio of at least 1:1 with respect to the second gas, preferably at least 3:2, 2:1, 3:1, 4:1, 5:1, or 10:1. Where the microbubble membrane is more permeable to the first gas than to the second gas (e.g., the membrane has respective permeabilities to the gases in a ratio of at least about 2:1, 3:1, 4:1, 5:1, or 10:1, preferably even higher, e.g., 20:1, 40:1, or 100:1), the bubbles advantageously shrink from their original first diameter to an average second diameter of 75% or less of their original diameter quite rapidly (e.g., within one, two, four, or five minutes). Then, when at least one relatively membrane-permeable gas is present in the aqueous medium comprising the continuous phase of the gas emulsion, the bubble is preferably stabilized at or about the second diameter for at least about 1 minute, preferably for 2, 3, 4, or 5 minutes. In one preferred embodiment, the bubbles maintain a size between about 5 or 6 μm and 1 μm for at least 1, 2, 3, 4, or 5 minutes, stabilized by a gas osmotic pressure differential. The gas tension in the external liquid is preferably at least about 700 mm Hg. Moreover, a relatively membrane impermeable gas is also in the microbubble to create such an osmotic pressure differential.

As stated above, the gas osmotic agent is preferably a gas that is less permeable through the bubble's surface than the modifier. It is also preferable that the gas osmotic agent is less soluble in blood and serum. Therefore, it will now be understood that the gas osmotic agent can be a gas at room or body temperature or it can ordinarily be a liquid at body temperature, so long as it has a sufficient partial or vapor pressure at the temperature of use to provide the desired osmotic effect.

Accordingly, fluorocarbons or other compounds that are not gases at room or body temperature can be used, provided that they have sufficient vapor pressure, preferably at least about 50 or 100 Torr at body temperature, or more preferably at least about 150 or 200 Torr. It should be noted that where the gas osmotic agent is a mixture of gases, the relevant measure of vapor pressure is the vapor pressure of the mixture, not necessarily the vapor pressure of the individual components of the mixed gas osmotic agent.

It is also important that where a perfluorocarbon is used as the osmotic agent within a bubble, the particular perfluorocarbon does not condense at the partial pressure present in the bubble and at body temperature. Depending on the relative concentrations of the primary modifier gas and the gas osmotic agent, the primary modifier gas may rapidly leave the bubble causing it to shrink and concentrate the secondary gas osmotic agent. Such shrinking may occur until the gas osmotic pressure equals the external pressure on the bubble (maximum absolute arterial pressure) plus the Laplace pressure of the bubble minus the air tension, or air saturation tension, of the blood (essentially one atmosphere). Thus the condensing partial pressure of the resulting gas mixture at 37° C. must be above the equilibrium partial pressure, discussed above, of the osmotic agent.

A Listing of some compounds possessing suitable solubility and vapor pressure criteria is provided in Table I:

TABLE I perfluoro propanes, $C_3F_8$
perfluoro butanes, $C_4F_{10}$
perfluoro cyclo butanes, $C_4F_8$
perfluoro pentanes, $C_5F_{12}$
perfluoro cyclo pentanes, $C_5F_{10}$
perfluoro methylcyclobutanes, $C_5F_{10}$
perfluoro hexanes, $C_6F_{14}$
perfluoro cyclohexanes, $C_6F_{12}$
perfluoro methyl cyclopentanes, $C_6F_{12}$
perfluoro dimethyl cyclobutanes, $C_6F_{12}$
perfluoro heptanes, $C_7F_{16}$
perfluoro cycloheptanes, $C_7F_{14}$
perfluoro methyl cyclohexanes, $C_7F_{14}$
perfluoro dimethyl cyclopentanes, $C_7F_{14}$
perfluoro trimethyl cyclobutanes, $C_7F_{14}$
perfluoro triethylamines, $N(C_2F_5)_3$ It will be appreciated that one of ordinary skill in the art can readily determine other compounds that would perform suitably in the present invention that do not meet both the solubility and vapor pressure criteria, described above. Rather, it will be understood that certain compounds can be considered outside the preferred range in either solubility or vapor pressure, if such compounds compensate for the aberration in the other category and provide a superior insolubility or high vapor pressure.

It should also be noted that for medical uses the gases, both the modifier gas and the gas osmotic agent, should be biocompatible or not be physiologically deleterious. Ultimately, the microbubbles containing the gas phase will decay and the gas phase will be released into the blood either as a dissolved gas or as submicron droplets of the condensed liquid. It will be understood that gases will primarily be removed from the body through lung respiration or through a combination of respiration and other pathways in the reticuloendothelial system.

A surprising discovery was that mixtures of PFCs, e.g., $C_4F_{10}$ (as a combination modifier gas and a gas osmotic agent) saturated with $C_6F_{14}$ vapor (as the main gas osmotic agent), can stabilize the bubble for longer times than either component alone. This is because $C_4F_{10}$ is a gas at body temperature (and, thus, can act as both a modifier gas and a gas osmotic agent) has a somewhat reduced membrane permeability and it is only slightly soluble in $C_6F_{14}$ at body temperature. In this situation the gas osmotic pressures of both agents are added together, leading to increased bubble persistence over that of air/$C_6F_{14}$ only mixtures. It is possible that the condensing point of the longer persisting higher molecular weight $C_6F_{14}$ component is increased, allowing a larger maximum gas osmotic pressure to be exerted. Other mixtures of PFCs will perform similarly. Preferred mixtures of PFCs will have ratios of 1:10 to 10:1, and include such mixtures as perfluorobutane/perfluorohexane and perfluorobutane/perfluoropentane. These preferred fluorochemicals can be branched or straight chain.

As was discussed above, we have also discovered that mixtures of nonosmotic gases in combination with the gas osmotic agent act to stabilize the size distribution of the bubbles before and after injection. Upon generation of the bubbles, the higher Laplace pressures in smaller bubbles causes diffusion through the liquid phase to the lower Laplace pressure larger bubbles. This causes the mean size distribution to increase above the capillary dimension limit of 5 microns with time. This is called disproportionation.

However, when a mixture of a modifier gases (e.g., air or carbon dioxide) are used with a gas osmotic agent (e.g., $C_6F_{14}$) a slight reduction in volume of the smaller bubbles, due to one of the modifier gases leaving the bubble, will concentrate the osmotic gas and increases its osmotic pressure, thus, retarding further shrinkage. On the other hand, the larger bubbles will increase in volume slightly, diluting the osmotic gas and also retarding further growth.

Accordingly, we have discovered that through use of a gas that is relatively hydrophobic and that has a relatively low membrane permeability, the rate of bubble decay can be reduced. Thus, through reducing the bubble decay rate, the microbubbles' half lives are increased and contrast enhancement potential is extended.

The desired gas is made to permeate the dry microspheres by placing the microspheres into a vial, which is placed in a vacuum chamber to evacuate the air. The air is then replaced with the desired gas or combination of gases (a preferred gas combination is nitrogen saturated with perfluorohexane at 13 degrees C.). The gas will then diffuse into the voids of the spheres. Diffusion can be aided by pressure or vacuum cycling. The vial is then crimp sealed and preferably sterilized with gamma radiation.

It will be appreciated that kits can be prepared for use in making the microbubble preparations of the present invention. These kits can include a container enclosing the gas or gases described above for forming the microbubbles, the liquid, and the surfactant. The container can contain all of the sterile dry components, and the gas, in one chamber, with the sterile aqueous liquid in a second chamber of the same container. Suitable two-chamber vial containers are available, for example, under the trademarks WHEATON RS177FLW or S-1702FL from Wheaton Glass Co., (Millville, N.J.). Such a container is illustrated in FIGS. 1–4. Referring to FIGS. 1 and 2, the illustrated Wheaton container 5 has an upper chamber 20 which can contain an aqueous solution 25, and a lower chamber 30 which can contain the dried ingredients 35 and a desired gas. A stopper 10 is provided separating the top chamber from the environment, and a seal 15 separates the upper chamber 20 from the lower chamber 30 containing spray dried (powdered) hollow microsphere 35 and the gas osmotic agent. Depressing the stopper 10 pressurizes the relatively incompressible liquid, which pushes the seal 15 downward into the lower chamber 30. This releases aqueous solution 25 into lower chamber 30, resulting in the dissolution of powder 35 to form stabilized microbubbles 45 containing the entrapped gas osmotic agent. Excess gas osmotic agent 40 is released from the lower chamber 30 into the upper chamber 20. This arrangement is convenient for the user and has the added unexpected advantage of sealing the small quantity of water-impermeable gas osmotic agent in the lower chamber by covering the interchamber seal with a thick (0.5 to 1.25 inch) layer of aqueous solution and the advantage that the aqueous solution can be introduced into the lower chamber without raising the pressure in the powder chamber by more than about 10%. Thus, there is no need for a pressure vent. (In contrast, conventional reconstitution of a solute in a single chamber vial with a needle and syringe without a vent can result in the production of considerable intrachamber pressure which could collapse the microbubbles.)

Figure 3:
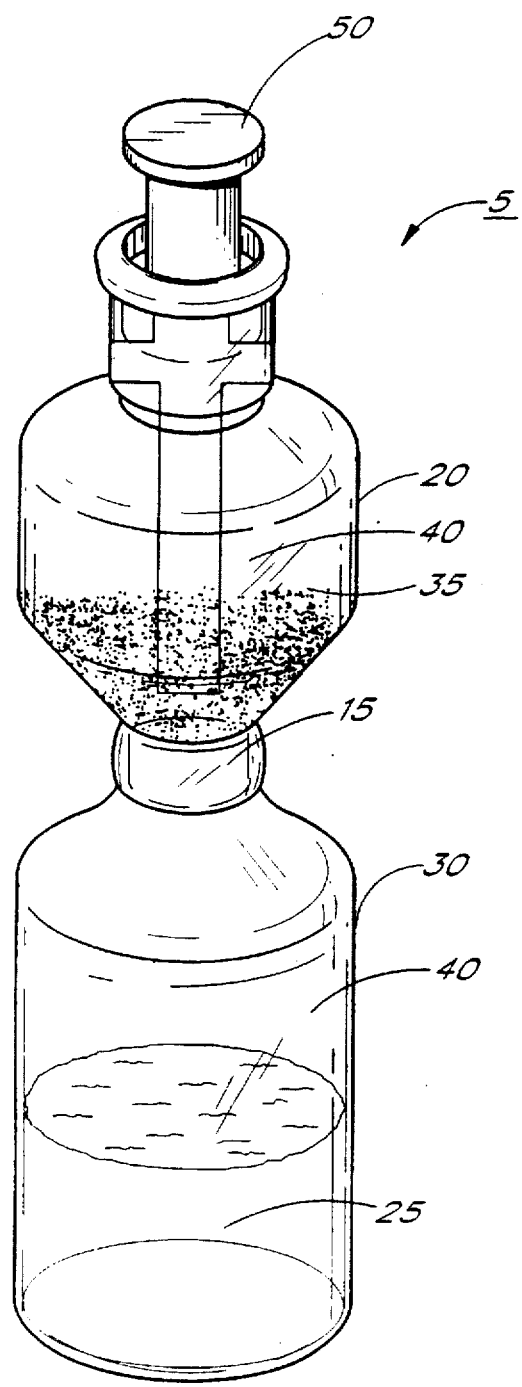
FIG. 3 is a perspective view of an inverted two-chamber vial containing a microbubble-forming preparation, with an aqueous solution in the lower chamber and solid and gaseous ingredients in the upper chamber.
Figure 4:
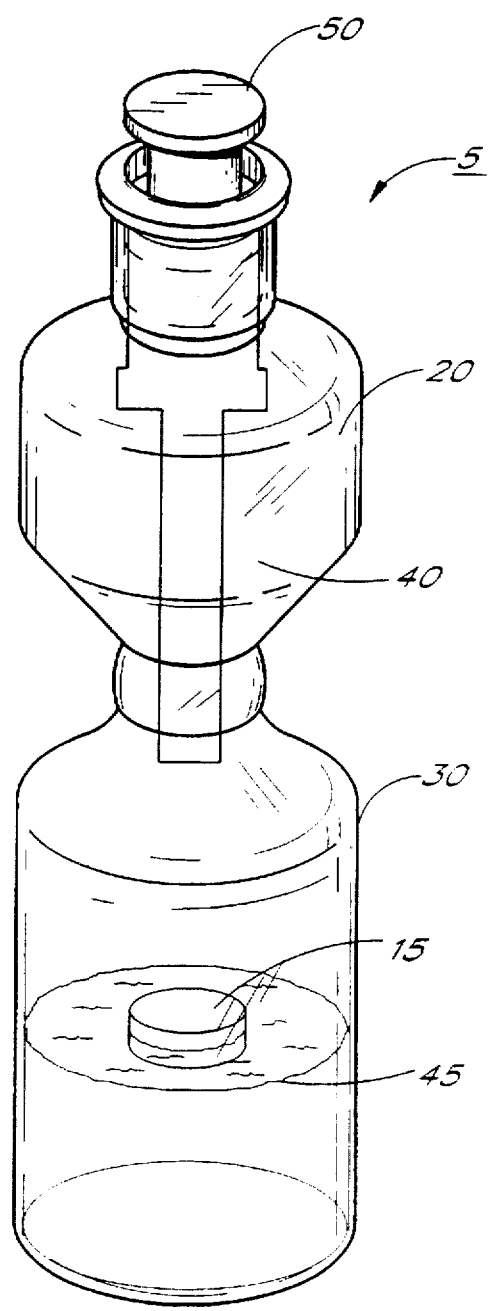
FIG. 4 illustrates the vial of FIG. 3, where the aqueous solution has been mixed with the solid ingredients to form microbubbles for administration to a patient.

Alternatively, an inverted two-chamber vial may be used for microbubble preparation. Referring to FIGS. 3 and 4, the same vial is used as described hereinabove, except that the stopper 50 is elongated such that it dislodges inner seal 15 when depressed. In this microbubble preparation method, the spray dried hollow microspheres 35 and the gas osmotic agent 40 are contained in the upper chamber 20. The aqueous solution 25 and gas osmotic agent 40 are contained within lower chamber 30. When stopper 50 is depressed, it dislodges seal 15 allowing the spray dried hollow microspheres to mix with the aqueous solution 25 in the presence of gas osmotic agent 40. One advantage associated with this method of microbubble formation is that the aqueous phase can be instilled first and sterilized via autoclaving or other means, followed by instillation of the spray dried microspheres. This will prevent potential microbial growth in the aqueous phase prior to sterilization.

Although one particular dual chamber container has been illustrated, other suitable devices are known and are commercially available. For example, a two compartment glass syringe such as the B-D HYPAK Liquid/Dry 5+5 ml Dual Chamber prefilled syringe system (Becton Dickinson, Franklin Lakes, N.J.; described in U.S. Pat. No. 4,613,326) can advantageously be used to reconstitute the spray dried powder. The advantages of this system include:

1. Convenience of use;
2. The aqueous-insoluble gas osmotic agent is sealed in by a chamber of aqueous solution on one side and an extremely small area of elastomer sealing the needle on the other side; and
3. a filtration needle such as Monoject #305 (Sherwood Medical, St. Louis, Mo.) can be fitted onto the syringe at the time of manufacture to ensure that no undissolved solids are injected.

The use of the two chamber syringe to form microbubbles is described in Example XIV.

It can be appreciated by one of ordinary skill in the art that other two-chamber reconstitution systems capable of combining the spray dried powder with the aqueous solution in a sterile manner are also within the scope of the present invention. In such systems, it is particularly advantageous if the aqueous phase can be interposed between the water-insoluble osmotic gas and the environment, to increase shelf life of the product. Where a material necessary for forming the microbubbles is not already present in the container, it can be packaged with the other components of the kit, preferably in a form or container adapted to facilitate ready combination with the other components of the kit.

Examples of particular uses of the microbubbles of the present invention include perfusion imaging of the heart, the myocardial tissue, and determination of perfusion characteristics of the heart and its tissues during stress or exercise tests, or perfusion defects or changes due to myocardial infarction. Similarly, myocardial tissue can be viewed after oral or venous administration of drugs designed to increase the blood flow to a tissue. Also, visualization of changes in myocardial tissue due to or during various interventions, such as coronary tissue vein grafting, coronary angioplasty, or use of thrombolytic agents (TPA or streptokinase) can also be enhanced. As these contrast agents can be administered conveniently via a peripheral vein to enhance the visualization of the entire circulatory system, they will also aid in the diagnosis of general vascular pathologies and in the ability to monitor the viability of placental tissue ultrasonically.

It should, however, be emphasized that these principles have application beyond ultrasound imaging. Indeed, the present invention is sufficiently broad to encompass the use of phospholipid-containing gas emulsions in any system, including nonbiological applications.

It will also be understood that other components can be included in the microbubble formulations of the present invention. For example, osmotic agents, stabilizers, chelators, buffers, viscosity modulators, air solubility modifiers, salts, and sugars can be added to modify the microbubble suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation.

Various embodiments of the present invention provide surprising advantages. The spray dried starch formulations provide prolonged in-vial stability, particularly when the molecular weight of the starch is over about 500,000. Fatty acid esters of sugars such as sucrose monostearate, as well as block copolymers such as Pluronic F-68 (with an HLB over 12) allow the powder to form bubbles at the instant they are rehydrated. Spray dried formulations with a structural agent such as a starch, starch derivative, or dextrin provide a significantly lower total dose of surfactant than comparable sonicated formulations. The use of two-chamber vials with water providing an additional seal for the gas osmotic agent provide increased shelf life, and greater use convenience. Spray dried formulations with a structural agent (such as a starch or dextrin), a hydrophobic phospholipid, and a more water soluble co-surfactant provide gas emulsions with greatly increased in vivo half lives.

Any of the microbubble preparations of the present invention may be administered to a vertebrate, such as a bird or a mammal, as a contrast agent for ultrasonically imaging portions of the vertebrate. Preferably, the vertebrate is a human, and the portion that is imaged is the vasculature of the vertebrate. In this embodiment, a small quantity of microbubbles (e.g., 0.1 ml/Kg [2 mg/Kg spray-dried powder] based on the body weight of the vertebrate) is introduced intravascularly into the animal. Other quantities of microbubbles, such as from about 0.005 ml/Kg to about 1.0 ml/Kg, can also be used. Imaging of the heart, arteries, veins, and organs rich in blood, such as liver and kidneys can be ultrasonically imaged with this technique.

The foregoing description will be more fully understood with reference to the following Examples. Such Examples, are, however, exemplary of preferred methods of practicing the present invention and are not limiting of the scope of the invention or the claims appended hereto.

EXAMPLE I

Spray drying of phospholipid-containing solution

One liter of the following solution was prepared in water for injection: 2.0% w/v Maltrin M-100 maltodextrin (Grain Processing Corp. Muscatine, Iowa), 0.95% w/v sodium chloride (Mallinckrodt, St. Louis, Mo.), 1.0% Superonic F-68 (Serva, Heidelberg, Germany), 1.0% w/v Ryoto Sucrose Stearate S-1670 (Mitsubishi-Kasei Food Corp., Tokyo, Japan), and 0.5% Lipoid E-100-3 hydrogenated phospholipid (Lipoid, Ludwigshafen, Germany).

This solution was then spray dried in a Niro Atomizer Portable Spray Dryer equipped with a two fluid atomizer (Niro Atomizer, Copenhagen, Denmark) employing the following settings:

| hot air flow rate | 39.5 CFM |
|---|---|
| inlet air temp. | 245° C. |
| outlet air temp. | 100° C. |
| atomizer air flow | 350 liters/min |
| liquid feed rate | 1 liter/hr |

The dry, hollow spherical product had a diameter between about 1 µM and about 15 µM and was collected at the cyclone separator as is standard for this dryer. Aliquots of powder (250 mg) were weighed into 10 ml tubing vials, evacuated and sparged with perfluorohexane-saturated nitrogen at 13° C. and sealed. The nitrogen was saturated with perfluorohexane by passing it through three perfluorohexane filled gas washing bottles immersed in a 13° C. water bath.

Upon reconstitution with 5 ml of water for injection, numerous bubbles were observed by light microscopy, ranging in size from 1 to 20 microns. The fact that many approximately 1 micron bubbles could be observed for an appreciable time demonstrates the added stability gained by including a phospholipid in the formula as an additional non-Newtonian viscoelastic surfactant.

EXAMPLE II

Comparison of phospholipid vs. sucrose ester gas emulsions

One liter of each of the following four solutions was prepared with water for injection:
Solution 1
3.9% w/v m-HES hydroxyethylstarch (Ajinimoto, Tokyo, Japan)
3.25% w/v Sodium chloride (Mallinckrodt, St. Louis, Mo.)
2.83% Sodium phosphate, dibasic (Mallinckrodt, St. Louis, Mo.)
0.42% w/v Sodium phosphate, monobasic (Mallinckrodt, St. Louis, Mo.)
Solution 2
2.11% w/v Poloxamer 188 (BASF, Parsipany, N.J.)
0.32% w/v Ryoto Sucrose Stearate S-1670 (Mitsubishi-Kasei Food Corp., Tokyo, Japan)
0.16% w/v Ryoto Sucrose Stearate S-570 (Mitsubishi-Kasei Food Corp., Tokyo, Japan)
Solution 3
3.6% w/v m-HES hydroxyethylstarch (Ajinimoto, Tokyo, Japan)
3.0% w/v Sodium chloride (Mallinckrodt, St. Louis, Mo.)
2.6% Sodium phosphate, dibasic (Mallinckrodt, St. Louis, Mo.)
0.39% w/v Sodium phosphate, monobasic (Mallinckrodt, St. Louis, Mo.)
Solution 4
0.15% w/v Poloxamer 188 (BASF, Parsipany, N.J.)
0.45% w/v Hydrogenated Egg phosphotidylcholine EPC-3 (Lipoid, Ludwigshafen, Germany)

Solutions 2 and 4 were added to high shear mixer and cooled in an ice bath. A coarse suspension of 3.0% v/v of 1,1,2-trichlorotrifluoroethane (Freon 113; EM Science, Gibbstown, N.J.) was made in the 1 liter of solutions 2 and 4. These suspensions were emulsified using a Microfluidizer (Microfluidics Corporation, Newton, Mass.; model M-110F) at 10,000 psi, 5° C. for 5 passes. The resulting emulsion 4 was added to solution 3 and the resulting emulsion 2 was added to solution 1. The Formula 1 and 2 mixture (containing sucrose ester surfactant) and the Formula 3 and 4 mixture (containing phospholipid surfactant) were then spray dried in a Niro Atomizer Portable Spray Dryer equipped with a two fluid atomizer (Niro Atomizer, Copenhagen, Denmark) employing the following settings:
Formula 1 and 2 mixture:

| hot air flow rate | 31 CFM |
|---|---|
| inlet air temp. | 370° C. |
| outlet air temp. | 120° C. |
| atomizer air flow | 290 liters/min |
| emulsion feed rate | 1.5 liter/hr |

Formula 3 and 4 mixture

| hot air flow rate | 31 CFM |
|---|---|
| inlet air temp. | 325° C. |
| outlet air temp. | 120° C. |
| atomizer air flow | 290 liters/min |
| emulsion feed rate | 1.5 liter/hr |

The dry, hollow spherical product had a diameter between about 1 µM and about 15 µM and was collected at the cyclone separator as is standard for this dryer. Aliquots of powder (250 mg) were weighed into 10 ml tubing vials, sparged with perfluorohexane-saturated nitrogen at 130° C. and sealed. The nitrogen was saturated with perfluorohexane by passing it through three perfluorohexane filled gas washing bottles immersed in a 13° C. water bath.

The vials were reconstituted with 5 ml water for injection after inserting an 18-gauge needle as a vent to relieve pressure as the water was injected. One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS.

While the sucrose ester formulation produced an initial ultrasound scatter signal 29% higher than the phospholipid formulation signal due to a higher microbubble concentration, surprisingly, the persistence of the phospholipid formulation was substantially longer. The sucrose ester formula signal decayed to 30% of its original signal in 140 seconds, while the phospholipid formula lasted for 550 seconds before decaying to the 30% signal level, demonstrating the superior persistence of a formula employing a phospholipid as the non-Newtonian viscoelastic surfactant.

EXAMPLE III

Comparison of water insoluble phospholipid vs. water insoluble phospholipid/water soluble surfactant (Poloxamer 188) microbubbles One liter of each of the following emulsions was prepared for spray drying as described in Example II:

Formulation A: Water Insoluble Phospholipid Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Hydrogenated Egg Phospholipids E PC 3, (Lipoid, Ludwigshafen, Germany)
3.0% v/v 1,1,2-Trichlorotrifluoroethane (Freon 113; EM Science, Gibbstown, N.J.)

Formulation B: Water Insoluble Phospholipid/Water Soluble (Poloxamer 188) Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Hydrogenated Egg Phospholipids E PC 3 (Lipoid, Ludwigshafen, Germany)
0.45% w/v Poloxamer 188 (BASF, Parsipany, N.J.)
3.0% v/v 1,1,2-trichlorotrifluoroethane (Freon 113; EM Science, Gibbstown, N.J.)

Upon reconstitution of 100 mg of the Formulation A spray dried powder with 5 mL water, approximately 20 million bubbles per mL were observed, ranging in size from 1 to 20 µm. Upon reconstitution of 100 mg of the Formulation B spray dried powder with 5 mL water, approximately 315 million bubbles (1575% more bubbles than in Formulation A) per mL were observed, ranging in size from 1 to 20 µm.

The addition of a relatively water soluble surfactant [HLB (Poloxamer 188) 29.0] to a water insoluble surfactant in the microbubble formulations significantly increased the concentration of bubbles formed, leading to a more efficacious ultrasound contrast agent. The HLB is a number between 0 and 40 assigned to emulsifying agents and substances which are emulsified. The HLB is indicative of emulsification behavior and is related to the balance between the hydrophilic and lipophilic portions of the molecule (Rosen, M., (1989), *Surfactants and Interfacial Phenomena*, Second Edition, John Wiley & Sons, New York, pp. 326–329).

EXAMPLE IV

Comparison of water insoluble phospholipid vs. water insoluble phospholipid/water soluble (Polysorbate 20) microbubbles One liter of each of the following emulsions was prepared for spray drying as described in Example II:

Formulation A: Water Insoluble Phospholipid Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Hydrogenated Egg Phospholipids E PC 3 (Lipoid, Ludwigshafen, Germany)
3.0% v/v 1,1,2-Trichlorotrifluoroethane (Freon 113; EM Science, Gibbstown, N.J.)

Formulation B: Water Insoluble Phospholipid/Water Soluble (Polysorbate 20) Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Hydrogenated Egg Phospholipids E PC 3 (Lipoid, Ludwigshafen, Germany)
0.15% w/v Polysorbate 20 (ICI, Wilmington, Del.)
3.0% v/v 1,1,2-Trichlorotrifluoroethane (Freon 113; EM Science, Gibbstown, N.J.)

Upon reconstitution of 100 mg of the Formulation A spray dried powder with 5 mL water, approximately 20 million bubbles per mL were observed, ranging in size from 1 to 20 µm. Upon reconstitution of 100 mg of the Formulation B spray dried powder with 5 mL water, approximately 250 million bubbles (1150% more bubbles than in Formulation A) per mL were observed, ranging in size from 1 to 20 µm.

In conclusion, the addition of the relatively water soluble surfactant, polysorbate 20 [HLB=16.7] to the water insoluble surfactant, hydrogenated phosphatidylcholine in the microbubble formulations significantly increased the concentration of bubbles formed, leading to a more efficacious ultrasound contrast agent.

EXAMPLE V

Gas emulsion prepared with a phospholipid combination

One liter of the following emulsion was prepared for spray drying as described in Example II:

3.6% w/v m-HES hydroxyethylstarch (Ajinimoto, Tokyo, Japan)
3.0% w/v Sodium chloride (Mallinckrodt, St. Louis, Mo.)
2.6% Sodium phosphate, dibasic (Mallinckrodt, St. Louis, Mo.)
0.39% w/v Sodium phosphate, monobasic (Mallinckrodt, St. Louis, Mo.)
0.22% w/v Dipalmitoylphosphatidylcholine (Genzyme, Cambridge, Mass.)
0.31% w/v Dioctanoylphosphatidylcholine (Avanti Polar Lipids, Alabaster, Ala.)
3.0% v/v of 1,1,2-Trichlorotrifluoroethane (Freon 113; EM Science, Gibbstown, N.J.)

Upon reconstitution with 5 ml water, approximately 51 million bubbles per ml were observed, ranging in size from 1 to 20 microns. The decay constant of the echogenic signal for this microbubble formulation was determined to be 0.0029 (1/sec).

One milliliter of this formulation was injected into the ear vein of a 2.5 kg New Zealand White Rabbit. The rabbit was subsequently imaged with an Acuson 128XP-5 ultrasound scanner equipped with a 5 MHz transducer. Upon infusion, the echogenicity of the blood vessels and chambers of the heart was intense and persisted for several minutes. In addition, the echogenicity of the myocardium and a solid organ such as the liver and kidney was homogeneously intense and persisted for several minutes. Notably, the echogenicity of the portal and hepatic veins were isointense, indicating minimal uptake by the reticuloendothelial phagocytic cells of the liver, resulting in prolonged vascular persistence.

EXAMPLE VI

Biocompatibility of Gas Emulsions Prepared from Mixed Long-Chain/Short-Chain Phospholipids One liter of the following emulsion was prepared for spray-drying as described in Example II:
3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate dibasic (Mallinckrodt, St. Louis, Mo.)
0.39% w/v Sodium phosphate monobasic (Mallinckrodt, St. Louis, Mo.)
0.22% w/v Dipalmitoylphosphatidylcholine (Syngena Ltd., Cambridge, Mass.)
0.31% w/v Dioctanoylphosphatidylcholine (Avanti Polar Lipids Inc., Alabaster, Ala.)
3.0% v/v 1,1,2-Trichlorotrifluoroethane (Freon 113; EM Science, Gibbstown, N.J.)

At these ratios of dipalmitoylphosphatidylcholine to dioctanoylphosphatidylcholine the surfactants form mixed micelles only. Upon reconstitution with 5 ml water, approximately 51 million gas emulsion droplets per ml were observed, ranging in size from 1 to 20 microns. The first order decay constant of the echogenic signal of the gas emulsion in rabbits at a dose of 5 mg/kg was determined to be 0.0029 $s^{-1}$. This corresponds to an intravascular half-life of 4 minutes.

The gas emulsion was assayed for complement activation using an in-vitro C3a diagnostic kit supplied by Quidel Corp. (San Diego, Calif.). No difference between the gas emulsion and the negative control (saline) were observed, indicating that the gas emulsion does not activate complement. It is well known that naked microbubbles activate complement.

| Sample Tested | [C3a] (ng/ml) |
| --- | --- |
| Zymosan (positive control) | 43403 |
| Saline (negative control) | 604 |
| gas emulsion | 412 |

The gas emulsion was also assayed for changes in hemodynamics in anesthetized dogs at a dose of 20 mg/kg. No changes in mean arterial pressure or pulmonary artery pressure were observed. These results indicate that no hemodynamic effects are observed with the gas emulsion at 10–100 times the clinically relevant dose.

| Time (minutes) | Mean Arterial Pressure (mmHg) | Pulmonary Artery Pressure (mmHg) |
| --- | --- | --- |
| 0 | 109.4 | 13.3 |
| 1 | 109.2 | 14.2 |
| 2 | 110.4 | 14.1 |
| 5 | 115.0 | 14.3 |
| 10 | 117.9 | 15.7 |
| 60 | 111.0 | 13.2 |
| 90 | 120.9 | 13.6 |

Thus, excellent efficacy and biocompatibility are provided in the same gas emulsion formulation.

EXAMPLE VII

Gas emulsion containing phospholipid supplemented with cholesterol

One half liter of each of the following solutions was prepared in water for injection. Solution 1 containing the starch and salts and Solution 2 containing the phospholipids and cholesterol dissolved in a mixture of the Freon 113 and ethanol. Solution 2 was added to a high shear mixer and cooled in an ice bath. A coarse suspension of 1,1,2 trichlorotrifluoroethane (Freon 113) was made by adding one half liter of water with vigorous agitation. This suspension was emulsified with Solution 2 as described in Example II. The resulting emulsion was added to solution 1 to produce the following formula for spray drying:
3.6% w/v m-HES hydroxyethylstarch (Ajinimoto, Tokyo, Japan)
3.0% w/v Sodium chloride (Mallinckrodt, St. Louis, Mo.)
2.6% Sodium phosphate, dibasic (Mallinckrodt, St. Louis, Mo.)
0.39% w/v Sodium phosphate, monobasic (Mallinckrodt, St. Louis, Mo.)
0.22% w/v Dipalmitoylphosphatidylcholine (Genzyme, Cambridge, Mass.)
0.31% w/v Dioctanoylphosphatidylcholine (Avanti Polar Lipids, Alabaster, Ala.)
0.05% w/v Cholesterol (Sigma, St. Louis, Mo.)
2.4% v/v of 1,1,2-Trichlorotrifluoroethane (EM Sciences, Gibbstown, N.J.)
0.6% v/v Ethanol (Spectrum Chemical, Gardena, Calif.)

This emulsion was then spray dried in a Niro Atomizer Portable Spray Dryer equipped with a two fluid atomizer (Niro Atomizer, Copenhagen, Denmark) employing the following approximate settings:

| hot air flow rate | 31 CFM |
| --- | --- |
| inlet air temp. | 325° C. |
| outlet air temp. | 120° C. |
| atomizer air flow | 290 liters/min |
| emulsion feed rate | 1.5 liter/hr |

The dry, hollow spherical product had a diameter between about 1 µM and about 15 µM and was collected at the cyclone separator as is standard for this dryer. Aliquots of powder (100 mg) were weighed into 10 ml tubing vials, sparged with perfluorohexane-saturated nitrogen at 13° C. and sealed as in Example II. The vials were reconstituted with 5 ml water for injection after inserting an 18-gauge needle as a vent to relieve pressure as the water was injected. A dose of 0.25 ml/kg of the resulting microbubble suspension was injected intravenously into an approximately 3 kg rabbit instrumented to monitor the Doppler ultrasound signal of its carotid artery, again, as in Example II. The signal 1 minute post injection was 0.71 volts with a decay constant of 0.010 $sec^{-1}$. Hematology samples were taken during the first 60 minutes post injection. No detectable drop in platelet count was observed nor detectable activation of complement per Example VI.

EXAMPLE VIII

In vivo efficacy of reconstituted lyophilized liposomes

A liposome forming solution with total lipid concentration of 50 mg/ml was prepared with hydrogenated soya lecithin (S PC-3, Lipoid, Ludwigshafen, Germany) and dicetyl phosphate (Sigma, St. Louis, Mo.) in 9:1 mole ratio. Following the Reverse-Phase Evaporation Method of Szoka and Papahadjopoulos in *Proc. Nat. Acad. Sci.* 75 USA (1978), 4194, the surfactants were dissolved in 120 ml of 1/1 v/v solution of diethyl ether/chloroform. 40 ml of deionized water was added. The mixture was sonicated for 10 minutes at 0–4 degrees C. with a 3 mm probe sonicator (50 W Vibra Cell, Sonics & Materials Inc., Danbury Conn.) to form an emulsion. A liposome dispersion was formed by removing the solvent under reduced pressure by rotary evaporation and filtering the solution through a 1.0 μm polycarbonate filter at 65 degrees C. 1 ml fractions of the liposome solution were then mixed with 4 ml of a 15% w/v maltose (Sigma, St. Louis) solution in 10 ml ultrasound vials, frozen at −30 degrees C., and lyophilized (FTS Systems, Stone Ridge, N.Y.). Vials were gassed with either nitrogen or nitrogen saturated with perfluorohexane at 13 degrees C. The lyophilized powder was reconstituted in 5 ml water to the following concentrations:

12.0% w/v Maltose (Sigma, St. Louis, Mo.)
0.928% w/v Hydrogenated Soya Lecithin S PC-3 (Lipoid, Ludwigshafen, Germany)
0.072% w/v Dicetyl phosphate (Sigma, St. Louis, Mo.)

One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood. Signals before contrast were less than 0.1 volts RMS.

Neither the nitrogen or the perfluorohexane gassed liposome containing formulations showed significant or lasting echogenicity in the rabbit model.

EXAMPLE IX

Effect of perfluorohexane gassing on ultrasound efficacy of lyophilized liposome formulations vs. spray dried gas emulsion formulations One liter of each of the following emulsions was prepared for spray drying as described in Example II:

Formulation A: Sucrose Ester Microbubble Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Sucrose ester 11025003 (Alliance Pharmaceutical Corp., San Diego, Calif.)
1.95% w/v Poloxamer 188 (BASF, Parsipany, N.J.)
3.0 v/v 1,1,2-Trichlorotrifluoroethane (Freon 113; EM Science, Gibbstown, N.J.)

Formulation B: Phospholipid Microbubble Formulation 3.6% w/v m-HES hydroxyethylstarch (Ajinimoto, Tokyo, Japan)
3.0% w/v Sodium chloride (Mallinckrodt, St. Louis, Mo.)
2.6% w/v Sodium phosphate, dibasic (Mallinckrodt, St. Louis, Mo.)
0.39% w/v Sodium phosphate, monobasic (Mallinckrodt, St. Louis, Mo.)
0.45% w/v Dipalmitoyl phosphatidylcholine (Genzyme Corp., Cambridge, Mass.)
0.15% w/v Poloxamer 188 (BASF, Parsipany, N.J.)
3.0% v/v 1,1,2-Trichlorotrifluoroethane (Freon 113; EM Science, Gibbstown, N.J.)

Formulation C: Lyophilized Liposome Formulation

Approximately 40 mL of a liposome dispersion containing hydrogenated soy lecithin and dicetyl phosphate (9:1 mole ratio) at a total lipid concentration of 50 mg/mL in water were prepared using the Reverse-Phase Evaporation Method (REV) described by Szoka and Papahadjopoulos (see Example VIII).

The formulation is summarized below:

|  | Dry Powder Formula (%, w/w) | Reconstituted for Injection (%, w/v) |
|---|---|---|
| Hydrogenated Soya Lecithin (Lipoid S PC-3, Lipoid, Ludwigshafen, Germany) | 7.14 | 0.928 |
| Dicetyl phosphate (Sigma, St. Louis, MO) | 0.55 | 0.072 |
| Maltose (Sigma, St. Louis, MO) | 92.3 | 12.0 |
| Water for injection |  | 5.0 mL |

Two vials were prepared of each of the formulations described above: one was gassed with a perfluorohexanenitrogen mixture; the other contained only nitrogen. The samples (6 total) were reconstituted with 5 mL water and evaluated for efficacy using a Pulsed Doppler Signal Enhancement Rabbit Model. Dosages administered to the rabbit were 5 mg of dry powder per kg of rabbit for formulations A, B and C, respectively.

The echogenic signals at 60 s for the nonperfluorohexane containing formulations A, B and C were 0.040, 0.142 and 0.005 V, respectively; the echogenic signals at 60 s for their respective perfluorohexane containing formulations were 1.232, 0.826 and 0 V. In conclusion, the addition of a perfluorohexane gassing step did not significantly increase the ultrasound efficacy (defined here as the echogenic signal at 60 s) of the lyophilized liposome formulation. Whereas the efficacy of the perfluorohexane containing spray dried sucrose ester microbubble and phospholipid microbubble formulations was increased by 2980% and 482%, respectively. Thus, fundamental differences in structure and behavior exist between the gas emulsions of the present invention and microbubble preparations made from lyophilized liposomes.

EXAMPLE X

Efficacy of spray dried dispersion containing the water insoluble phospholipid described in Example 4 of U.S. Pat. No. 5,380,519 to Schneider, et al.

A formulation containing the proportions of phospholipid and dicetyl phosphate as described in Example 4 of U.S. Pat. No. 5,380,519 to Schneider, et al. was prepared by spray drying the following emulsion. The surfactants were not laminarized (converted to liposomes) as in the Schneider example.

One liter of each of the following solutions was prepared with water for injection: Solution 1 containing the starch and salts and Solution 2 containing the surfactants. Solution 2 was added to a high shear mixer and cooled in an ice bath. A coarse suspension of 1,1,2-trichlorotrifluoroethane (Freon 113) was made in the 1 liter of solution 2. This suspension was emulsified using a Microfluidizer (Microfluidics Corporation, Newton, Mass.; model M-110F) at 10,000 psi, 5° C. for 5 passes. The resulting emulsion was added to solution 1 to produce the following formula for spray drying:

3.6% w/v m-HES Hydroxyethylstarch (Ajinomoto Corp. Tokyo, Japan)
3.0% w/v Sodium chloride (Mallinckrodt, St. Louis, Mo.)
2.6% w/v Sodium Phosphate, dibasic (Mallinckrodt, St. Louis, Mo.)
0.39% w/v Sodium Phosphate, monobasic (Mallinckrodt, St. Louis, Mo.)
0.058% w/v Dicetyl phosphate (Sigma, St. Louis, Mo.)
0.742% w/v Phospholipid PC-3 (Lipoid, Ludwigshafen, Germany)
3.0% v/v 1,1,2-trichlorotrifluoroethane (EM Sciences, Gibbstown, N.J.)

This emulsion was then spray dried in a Niro Atomizer Portable Spray Dryer equipped with a two fluid atomizer (Niro Atomizer, Copenhagen, Denmark) employing the following approximate settings:

hot air flow rate=31 CFM inlet air temp.=325° C.

outlet air temp.=120° C.

atomizer air flow=290 liters/min emulsion feed rate=1.5 liter/hr

The dry, hollow spherical product had a diameter between about 1 µM and about 15 µM and was collected at the cyclone separator as is standard for this dryer. Aliquots of powder (100 mg) were weighed into 10 ml tubing vials, sparged with nitrogen only or nitrogen plus perfluorohexane (PFH) and sealed as in the above examples.

The vials were reconstituted with 5 ml water for injection after inserting an 18-gauge needle as a vent to relieve pressure as the water was injected. One ml of the resulting microbubble suspension was injected intravenously into an approximately 3 kg rabbit instrumented to monitor the Doppler ultrasound signal of its carotid artery, as in the previous examples.

Signals were observed with both with and without PFH. The PFH containing agent produced a signal of 0.08 volts at 60 seconds with a 0.02 volt signal at 200 seconds. The nitrogen only agent produced a signal of 0.2 volts at 60 seconds with a 0.04 volt signal at 200 seconds. As this formula does not contain a more water soluble surfactant, the signals are far inferior to the previous examples. The spray drying process did however present this non laminarized surfactant mixture in a physical state which produced detectable signals, unlike the laminarized formula of the Schneider et al. Example 4, as demonstrated in Example VIII above. This formula also differs from the other examples of this application in that the addition of perfluorohexane reduced the resultant signal rather than greatly enhancing it.

EXAMPLE XI

Non-fluorocarbon containing microbubbles

Two formulations were prepared (A. Mixed Phospholipid and B. Phospholipid+Poloxamer 188) by spray drying the following emulsions with a similar process.

One liter of each of the following solutions was prepared with water for injection: Solution 1 containing the starch and salts and Solution 2 containing the surfactants. Solution 2 was added to a high shear mixer and cooled in an ice bath. A coarse suspension of 1,1,2-trichlorotrifluoroethane (Freon 113) was made in the 1 liter of solution 2. This suspension was emulsified using a Microfluidizer (Microfluidics Corporation, Newton, Mass.; model M-110F) at 10,000 psi, 5° C. for 5 passes. The resulting emulsion was added to solution 1 to produce the following formula for spray drying:

Formula A (Mixed Phospholipid)

3.6% w/v m-HES Hydroxyethylstarch (Ajinomoto Corp. Tokyo, Japan)
3.0% w/v Sodium chloride (Mallinckrodt, St. Louis, Mo.)
2.6% w/v Sodium Phosphate Dibasic (Mallinckrodt, St. Louis, Mo.)
0.39% w/v Sodium Phosphate, monobasic (Mallinckrodt, St. Louis, Mo.)
0.22% w/v Dipalmitoyl phosphotidal choline (Genzyme, Cambridge, Mass.)
0.31% w/v Dioctinoyl phosphotidal choline (Genzyme, Cambridge, Mass.)
3.0% v/v 1,1,2-trichlorotrifluoroethane (EM Sciences, Gibbstown, N.J.)

Formula B (Phospholipid+Poloxamer 188)

3.6% w/v m-HES Hydroxyethylstarch (Ajinomoto Corp. Tokyo, Japan)
3.0% w/v Sodium chloride (Mallinckrodt, St. Louis, Mo.)
2.6% w/v Sodium phosphate dibasic (Mallinckrodt, St. Louis, Mo.)
0.39% w/v Sodium Phosphate Monobasic (Mallinckrodt, St. Louis, Mo.)
0.15% w/v Poloxamer 188 (BASF, Parsipany, N.J.)
0.45% w/v Phospholipid PC-3 (Lipoid, Ludwigshafen, Germany)
3.0% v/v 1,1,2-trichlorotrifluoroethane (EM Sciences, Gibbstown, N.J.)

This emulsion was then spray dried in a Niro Atomizer Portable Spray Dryer equipped with a two fluid atomizer (Niro Atomizer, Copenhagen, Denmark) employing the following approximate settings:

hot air flow rate=31 CFM inlet air temp.=325° C.

outlet air temp.=120° C.

atomizer air flow=290 liters/min emulsion feed rate=1.5 liter/hr

The dry, hollow spherical product had a diameter between about 1 µM and about 15 µM and was collected at the cyclone separator as is standard for this dryer. Aliquots of powder (100 mg) were weighed into 10 ml tubing vials, sparged with nitrogen only and sealed.

The vials were reconstituted with 5 ml water for injection after inserting an 18-gauge needle as a vent to relieve pressure as the water was injected. One ml of the resulting microbubble suspension was injected intravenously into an approximately 3 kg rabbit instrumented to monitor the Doppler ultrasound signal of its carotid artery. A 10 MHz flow cuff (Triton Technology Inc., San Diego, Calif.; model ES-10-20) connected to a System 6 Doppler flow module (Triton Technology Inc.) fed the RF doppler signal to a LeCroy 9410 oscilloscope (LeCroy, Chestnut Ridge, N.Y.). The root mean square (RMS) voltage of the signal computed by the oscilloscope was transferred to a computer and the resultant curve fitted to obtain peak echogenic signal intensity and half-life of the microbubbles in blood.

Significant signals were observed with both formulas. Formula A produced a signal of 0.25 volts at 60 seconds with a 0.13 volt signal at 200 seconds. Formula B produced a signal of 0.3 volts at 60 seconds with a 0.2 volt signal at 200 seconds. Non-phospholipid formulas produce only background signals when treated the same fashion.

As has been described above, this may be the result of water first contacting the inside surface of the spherical cavity (0.5–10 microns diameter) after percolating through the dissolving surfactants and structural agents resulting in the formation of a bubble of the desired size (the size of the cavity) surrounded initially by saturated surfactant solution and therefore having an optimal maximally packed surfactant coating, enhancing gas entrapment. Such bubbles are remarkably stable in-vivo even when filled with water soluble gases (e.g. air or nitrogen).

EXAMPLE XII

Effect of phospholipid acyl chain length on ultrasound echogenic efficacy

One liter of each of the following emulsions was prepared for spray drying as described in Example II:

Formulation A: Dimyristoyl Phosphatidylcholine Formulation 3.6% w/v m-HES hydroxyethylstarch (Ajinimoto, Tokyo, Japan)
3.0% w/v sodium chloride (Mallinckrodt, St. Louis, Mo.)
2.6% w/v sodium phosphate, dibasic (Mallinckrodt, St. Louis, Mo.)
0.39% w/v sodium phosphate, monobasic (Mallinckrodt, St. Louis, Mo.)
0.45% w/v Dimyristoyl phosphatidylcholine (Genzyme Corp., Cambridge, Mass.)
0.15% w/v Poloxamer 188 (BASF, Parsipany, N.J.)
3.0% v/v 1,1,2-trichlorotrifluoroethane (Freon 113; EM Science, Gibbstown, N.J.)

Formulation B: Distearoyl Phosphatidylcholine Formulation 3.6% w/v m-HES hydroxyethylstarch (Ajinimoto, Tokyo, Japan)
3.0% w/v sodium chloride (Mallinckrodt, St. Louis, Mo.)
2.6% w/v sodium phosphate, dibasic (Mallinckrodt, St. Louis, Mo.)
0.39% w/v sodium phosphate, monobasic (Mallinckrodt, St. Louis, Mo.)
0.45% w/v Distearoyl phosphatidylcholine (Genzyme Corp., Cambridge, Mass.)
0.15% w/v Poloxamer 188 (BASF, Parsipany, N.J.)
3.0% v/v 1,1,2-trichlorotrifluoroethane (Freon 113; EM Science, Gibbstown, N.J.)

After reconstitution with 5 ml water, the two formulations were evaluated for efficacy using a Pulsed Doppler Signal Enhancement Rabbit Model as in Example II and the echogenic signal measured as a function of time. Dosages administered to the rabbit were 5 mg of dry powder per kg of rabbit.

| | Time (s) | | | | | | | |
|---|---|---|---|---|---|---|---|---|
| | 20 | 60 | 100 | 200 | 300 | 400 | 500 | 600 |
| Formul. A Echogenic signal (V) | 0.8 | 0.6 | 0.5 | 0.4 | 0.4 | 0.4 | 0.3 | 0.2 |

-continued

| | Time (s) | | | | | | | |
|---|---|---|---|---|---|---|---|---|
| | 20 | 60 | 100 | 200 | 300 | 400 | 500 | 600 |
| Formul. B Echogenic Signal (V) | 0.5 | 0.4 | 0.2 | 0.2 | 0.1 | 0.1 | 0.1 | 0.1 |

The echogenic signal as a function of time was on average greater for the formulation containing dimyristoyl phosphatidylcholine (DMPC) than for the formulation containing distearoyl phosphatidylcholine (DSPC). Both fatty acid ester chains of DMPC contain 14 carbons, whereas the fatty acid ester chains are both 18 carbons in length or DSPC. This chain length difference between the two phospholipid compounds results in a different gel to liquid-crystal phase transition temperature. At temperatures above this transition temperature the hydrocarbon chains are in the melted state and the phospholipids form a liquid crystal phase. This transition temperature is 55.5° C. for DSPC and 23.5° C. for DMPC in water.

Therefore, the use of a phospholipid first surfactant which is in the liquid crystal state after injection (Rabbit body temperature=appx. 37.5° C.) can be advantageous.

EXAMPLE XIII

Microbubble formation using two chamber vial 800 mg of spray dried powder was weighed into the lower chamber of a 20 ml Wheaton RS-177FLW two chamber vial (FIG. 1). The vial was flushed with perfluorohexane-saturated nitrogen at 13° C. before inserting the interchamber seal. The upper chamber was filled with 10 ml sterile water for injection. The upper chamber stopper was inserted so as to eliminate all air bubbles in the upper chamber. Upon depression of the upper stopper, the interchamber seal was forced into the lower chamber, allowing the water to flow into the lower chamber and reconstitute the powder (FIG. 2). Numerous stable microbubbles were formed as demonstrated by light microscopy. This procedure demonstrates the convenience of this form of packaging and the elimination of the need to provide a vent to eliminate pressure buildup when the aqueous phase is added to the powder.

EXAMPLE XIV

Microbubble formation using two chamber syringe

One hundred mg of spray dried powder was weighed into a 5 ml+5 ml HYPAK Liquid/Dry dual chamber syringe (Becton Dickinson, Franklin Lakes, N.J.) and shaken into the powder (needle end) chamber. The interchamber seal was then positioned just above the bypass channel. A 5 µM filter-containing needle was then fitted on the syringe. The powder-containing chamber was then filled with the gas osmotic agent by placing the assembly in a vacuum chamber, evacuating and refilling the chamber with the gas osmotic agent, perfluorohexane-saturated nitrogen at 13° C. The filter needle allows the evacuation and refilling of the atmosphere in the powder-containing chamber. A sealing needle cover was then placed on the needle. The liquid chamber was then filled with 4 ml water for injection and the plunger was seated using a temporary vent (wire inserted between the glass syringe barrel and the plunger so as to eliminate all air bubbles.

To reconstitute, the needle sealing cover was removed to eliminate pressure buildup in the powder chamber. The plunger was then depressed, forcing the interchamber seal to the bypass position which allowed the water to flow around the interchamber seal into the powder-containing chamber. The plunger motion was stopped when all the water was in the powder chamber. The syringe was agitated to dissolve the powder. Excess gas and any large bubbles were expelled by holding the syringe, needle end up, and further depressing the plunger. The solution containing numerous stabilized microbubbles (as observed by light microscopy) was then expelled from the syringe by depressing the plunger to its limit.

The foregoing description details certain preferred embodiments of the present invention and describes the best mode contemplated. It will be appreciated, however, that no matter how detailed the foregoing appears in text, the invention can be practiced in many ways and the invention should be construed in accordance with the appended claims and any equivalents thereof.

What is claimed is:

1. A method for forming a gas emulsion comprising the steps of:
providing a container having therein a substantially non-lamellar approximately microspherical material comprising at least a first and a second surfactant, a hydrophilic monomer or polymer or combination thereof, and a gas or gas mixture, said first surfactant comprising a phospholipid or mixture of phospholipids having at least one acyl chain which comprises at least 10 carbon atoms, and comprising at least about 5% w/w of total surfactant, said second surfactant being more water soluble than said first surfactant;
adding an aqueous liquid to said container;
substantially dissolving said microspherical material in said aqueous liquid, thereby forming a gas emulsion in said container, said gas emulsion comprising bubbles of said gas or gas mixture surrounded by a layer of said first and said second surfactants said gas emulsion substantially free of lamellar surfactant structures.

2. The method of claim 1, wherein said second surfactant is selected from the group consisting of a fatty acid, a salt of a fatty acid, a sugar ester of a fatty acid, a polyoxypropylene-polyoxyethylene copolymer, a nonionic alkylglucoside, a polysorbate, and combinations thereof.

3. The method of claim 1, wherein said second surfactant is selected from the group consisting of a phospholipid, a mixture of phospholipids, a phosphocholine, a lysophospholipid and combinations thereof wherein each acyl chain comprises no more than 14 carbon atoms.

4. The method of claim 1, wherein said first surfactant is a phosphatidylcholine with one or more acyl chains, at least one chain comprising 12 to 18 carbon atoms, and said second surfactant is a phosphatidylcholine with one or more acyl chains, at least one chain comprising 6 to 12 carbon atoms.

5. The method of claim 1, wherein said hydrophilic monomer or polymer or combination thereof is selected from the group consisting of starches, derivatized starches and combinations thereof.

6. The method of claim 1, wherein said gas or gas mixture comprises a gas osmotic agent and a modifier gas.

7. The method of claim 6, wherein said gas osmotic agent has a vapor pressure of less than 760 mm Hg at 37 degrees C.

8. The method of claim 6 wherein said modifier gas comprises a compound selected from the group consisting of nitrogen oxygen, carbon dioxide and combinations thereof.

9. The method of claim 6 wherein said gas osmotic agent is selected from the group consisting of perfluoropropane, perfluorobutane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

10. The method of claim 9 wherein said modifier gas is air.

11. The method of claim 9 wherein said gas osmotic agent is perfluorohexane.

12. The method of claim 11 wherein said modifier gas is nitrogen.

13. A method for imaging an object or body comprising the steps of:
introducing a gas emulsion made according to the method of claim 1 into said object or body, and;
ultrasonically imaging at least a portion of said object or body.

14. A method for imaging an object or body comprising the steps of:
introducing a gas emulsion made according to the method of claim 6 into said object or body, and;
ultrasonically imaging at least a portion of said object or body.

15. A method for imaging an object or body comprising the steps of:
introducing a gas emulsion made according to the method of claim 9 into said object or body, and;
ultrasonically imaging at least a portion of said object or body.

16. A method for imaging an object or body comprising the steps of:
introducing a gas emulsion made according to the method of claim 12 into said object or body, and;
ultrasonically imaging at least a portion of said object or body.

17. A gas emulsion ultrasound contrast medium, comprising:
an aqueous continuous phase substantially free of lamellar surfactant structures comprising a plurality of bubbles of a gas or gas mixture comprising a fluorocarbon or mixture of fluorocarbons having at least four carbon atoms surrounded by a surfactant layer comprising at least a first and a second surfactant, said first surfactant consisting essentially of a phospholipid or mixture of phospholipids having at least one acyl chain which comprises at least 10 carbon atoms, and comprising at least about 5% w/w of total surfactant, and wherein said second surfactant is more water soluble than said first surfactant.

18. The contrast medium of claim 17, wherein said second surfactant is selected from the group consisting of a fatty acid, a salt of a fatty acid, a sugar ester of a fatty acid, a polyoxypropylene-polyoxyethylene copolymer, a nonionic alkylglucoside, a polysorbate, and combinations thereof.

19. The contrast medium of claim 17, wherein said second surfactant is selected from the group consisting of a phospholipid, a mixture of phospholipids, a phosphocholine, a lysophospholipid and combinations thereof wherein each acyl chain comprises no more than 14 carbon atoms.

20. The contrast medium of claim 17, wherein said first surfactant is a phoshatidylcholine with one or more acyl chains, at least one chain comprising 12 to 18 carbon atoms, and said second surfactant is a phosphatidylcholine with one or more acyl chains, at least one chain comprising 6 to 12 carbon atoms.

33

21. The contrast medium of claim 17, wherein said gas or gas mixture comprises a gas osmotic agent and a modifier gas.

22. The contrast medium of claim 21, wherein said modifier gas comprises a compound selected from the group consisting of nitrogen, oxygen, carbon dioxide and combinations thereof.

23. A method for imaging an object or body comprising the steps of:

introducing an ultrasound contrast medium according to claim 17 into said object or body, and;

ultrasonically imaging at least a portion of said object or body.

24. A method for imaging an object or body comprising the steps of:

introducing an ultrasound contrast medium according to claim 22 into said object or body, and;

ultrasonically imaging at least a portion of said object or body.

25. The contrast medium of claim 21 wherein said gas osmotic agent is selected from the group consisting of perfluoropropane, perfluropropane, perfluorocyclobutane, perfluoromethylcyclobutane, perfluoropentane, perfluorocyclopentane, perfluoromethylcyclopentane, perfluorodimethylcyclobutanes, perfluorohexane, perfluorocyclohexane, perfluoroheptane, perfluorocycloheptane, perfluoromethylcyclohexane, perfluorodimethylcyclopentane, perfluorotrimethylcyclobutane, and perfluorotriethylamine.

26. The contrast medium of claim 25 wherein said gas osmotic agent is perfluorohexane.

27. The contrast medium of claim 25 wherein said modifier gas is air.

28. A method for imaging an object or body comprising the steps of:

introducing an ultrasound contrast medium according to claim 25 into said object or body, and;

ultrasonically imaging at least a portion of said object or body.

29. A method for imaging an object or body comprising the steps of:

introducing an ultrasound contrast medium according to claim 26 into said object or body, and;

ultrasonically imaging at least a portion of said object or body.

30. The contrast agent of claim 26 wherein said modifier gas is nitrogen.

31. A method for imaging an object or body comprising the steps of:

34 introducing an ultrasound contrast medium according to claim 30 into said object or body, and;

ultrasonically imaging at least a portion of said object or body.

32. A method of making an ultrasound contrast medium comprising substantially dissolving a substantially non-lamellar composition in an aqueous liquid thereby forming a gas emulsion substantially free of lamellar surfactant structures, said gas emulsion comprising bubbles containing said gas or gas mixture surrounded by a layer of said first and said second surfactants wherein said first surfactant is a phospholipid or mixture of phospholipids having at least one acyl chain which comprises at least 10 carbon atoms, and comprising at least about 5% w/w of total surfactant, and said second surfactant is more water soluble than said first surfactant.

33. A method of making an ultrasound contrast medium comprising substantially dissolving a composition associated with a gas mixture comprising perfluorohexane and a modifier gas selected from the group consisting of nitrogen, oxygen, carbon dioxide and combinations thereof in an aqueous liquid, thereby forming a gas emulsion in said container, said gas emulsion comprising bubbles containing said gas mixture surrounded by a layer of said first and said second surfactants wherein said first surfactant is a phospholipid or mixture of phospholipids having at least one acyl chain which comprises at least 10 carbon atoms, and comprising at least about 5% w/w of total surfactant, and said second surfactant is more water soluble than said first surfactant.

34. A method for imaging an object or body comprising the steps of:

introducing an ultrasound contrast medium made according to the method of claim 33 into said object or body, and;

ultrasonically imaging at least a portion of said object or body.

35. A gas emulsion ultrasound contrast medium, comprising:

an aqueous continuous phase substantially free of lamellar surfactant structures comprising a plurality of bubbles of a gas or gas mixture comprising a fluorocarbon or mixture of fluorocarbons surrounded by a surfactant layer comprising dimyristoyl phosphatidylcholine and a second surfactant wherein said second surfactant is more water soluble than dimyristoyl phosphatidylcholine.

* * * * *

UNITED STATES PATENT AND TRADEMARK OFFICE
CERTIFICATE OF CORRECTION

PATENT NO. : 5,798,091
DATED : August 25, 1998
INVENTOR(S) : Trevino et al.

It is certified that error appears in the above-identified patent and that said Letters Patent is hereby corrected as shown below:

Title page, item [63] please delete "Ser. No. 99,953, Jul. 30,1993, Pat. No. 5,414,600." and insert --Ser. No, 99,951, Jul. 30,1993, now abandoned.--

Signed and Sealed this

Twenty-seventh Day of July, 1999

Attest:

Q. TODD DICKINSON

Attesting Officer     Acting Commissioner of Patents and Trademarks